United States Patent [19]

Bacus

[11] 4,453,266
[45] Jun. 5, 1984

[54] METHOD AND APPARATUS FOR MEASURING MEAN CELL VOLUME OF RED BLOOD CELLS

[75] Inventor: James W. Bacus, Hinsdale, Ill.

[73] Assignee: Rush-Presbyterian-St. Luke's Medical Center, Chicago, Ill.

[21] Appl. No.: 142,124

[22] Filed: Apr. 21, 1980

[51] Int. Cl.$^3$ .............................................. G06K 9/00
[52] U.S. Cl. .......................................... 382/6; 356/39
[58] Field of Search ................................ 235/92 PC; 340/146.3 CA, 146.3 AC, 146.3 R; 356/39; 364/416, 515; 382/6

[56] References Cited

U.S. PATENT DOCUMENTS

| | | | |
|---|---|---|---|
| 2,656,508 | 10/1953 | Coulter | 235/92 PC |
| 3,259,842 | 7/1966 | Coulter et al. | 235/92 PC |
| 3,851,156 | 11/1974 | Green | 364/416 |
| 3,944,797 | 3/1976 | Coulter et al. | 235/92 PC |
| 3,982,183 | 9/1976 | Collineau et al. | 235/92 PC |
| 4,052,596 | 10/1977 | Vick | 235/92 PC |
| 4,063,309 | 12/1977 | Hennessy et al. | 235/92 PC |
| 4,086,631 | 4/1978 | Vick | 235/92 PC |
| 4,097,845 | 6/1978 | Bacus | 235/92 PC |
| 4,128,884 | 12/1978 | England | 235/92 PC |

*Primary Examiner*—Leo H. Boudreau
*Attorney, Agent, or Firm*—Fitch, Even, Tabin & Flannery

[57] ABSTRACT

An apparatus and method are provided for producing signals representative of the mean cell volume of red blood cells in a blood specimen. The apparatus includes means for generating signals repesentative of the area of the cells and means for measuring the optical density of the individual cells and for generating signals representative of the hemoglobin content or mass of the cells. The central pallor is measured for cells having central pallors and means generate a signal representative of the central pallor of these cells. The representative area signals, hemoglobin signals and central pallor signals are sent to a means which generates an output representative of the mean cell volume of the cells.

25 Claims, 26 Drawing Figures

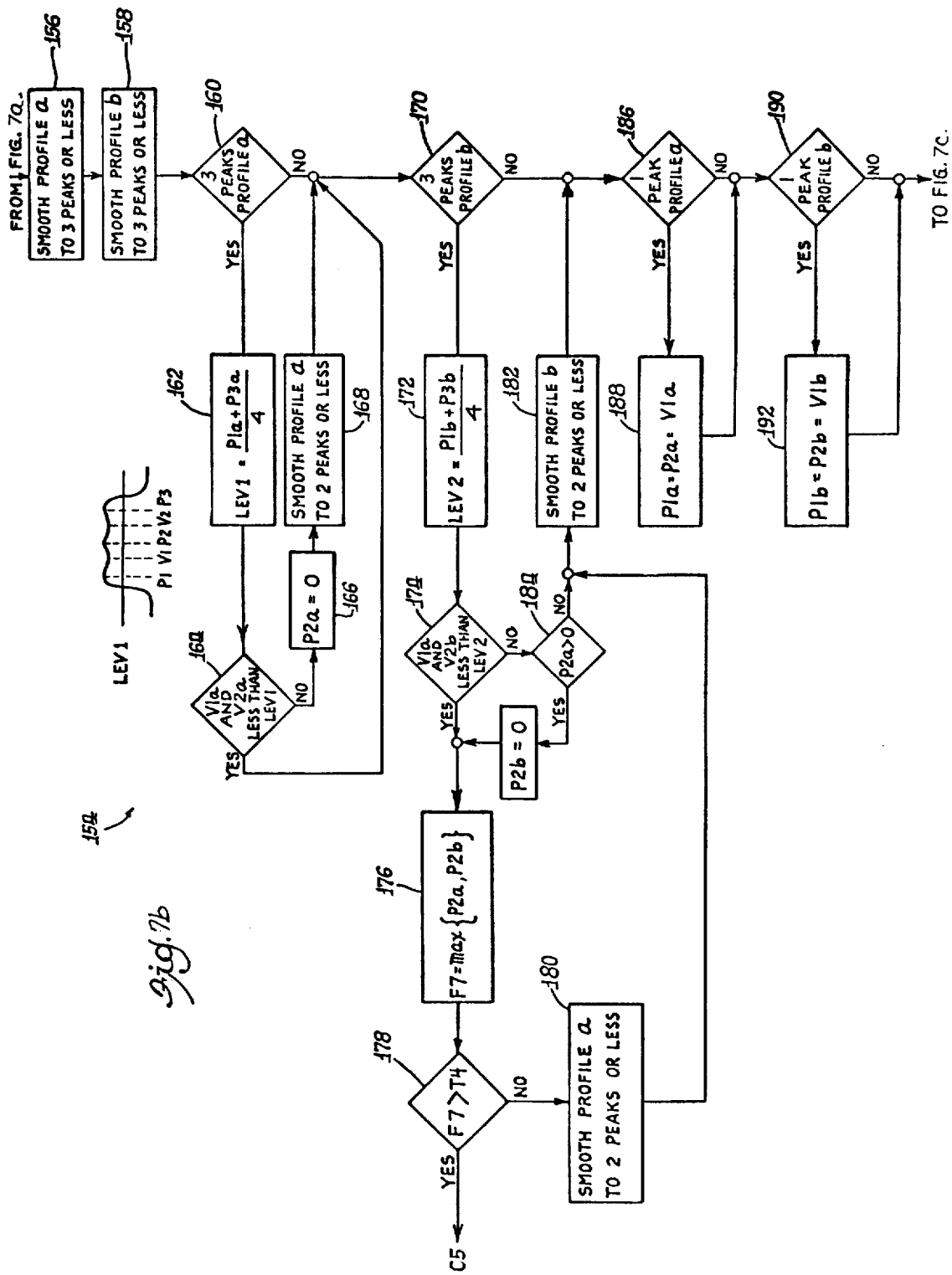

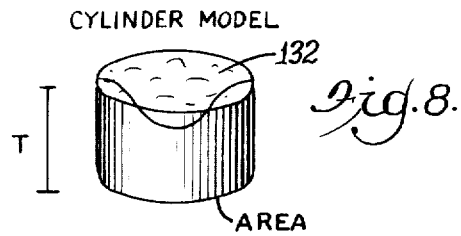
Fig. 8.
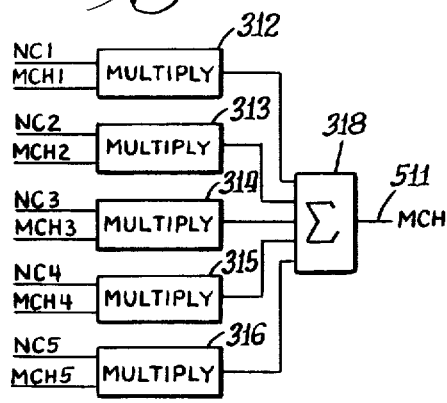
Fig. 14e.
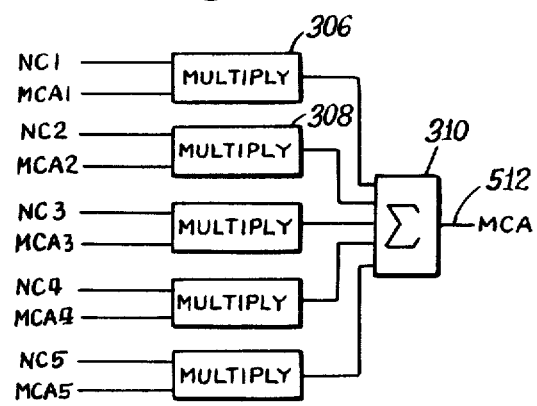
Fig. 14d.
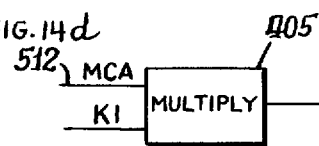
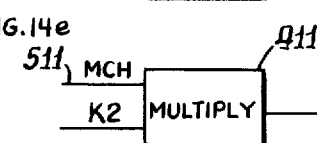
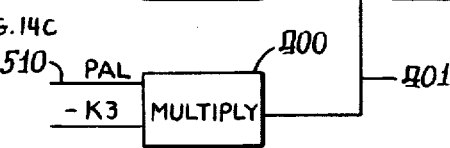
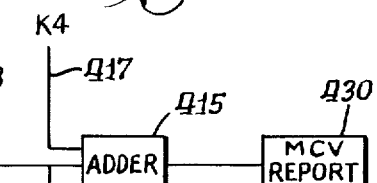
Fig. 15.

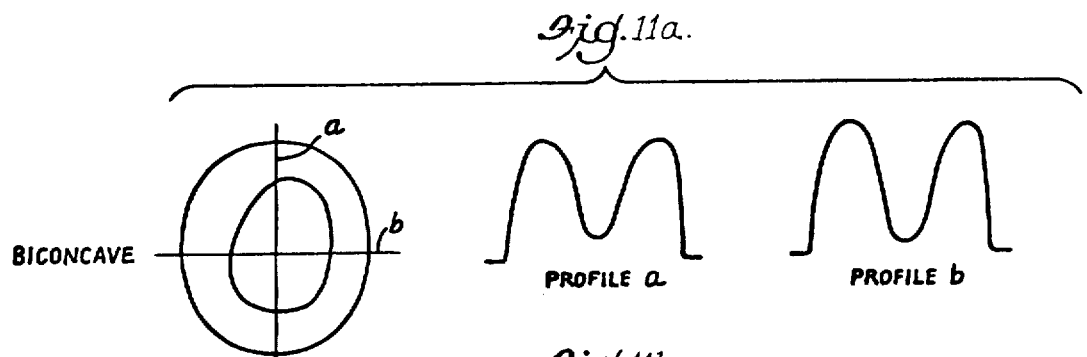
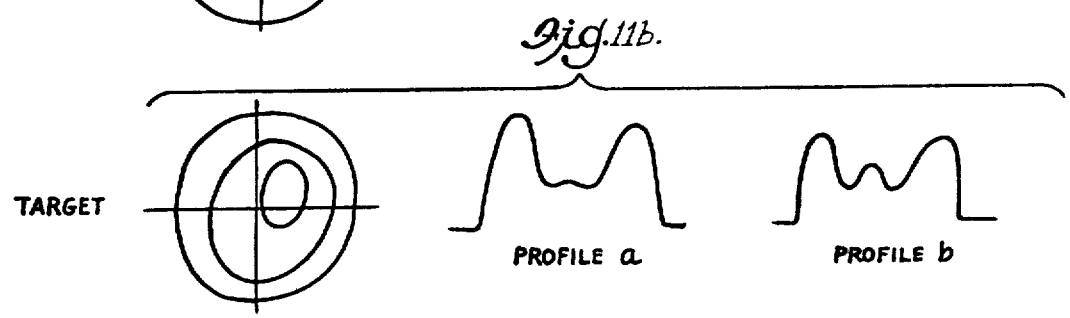
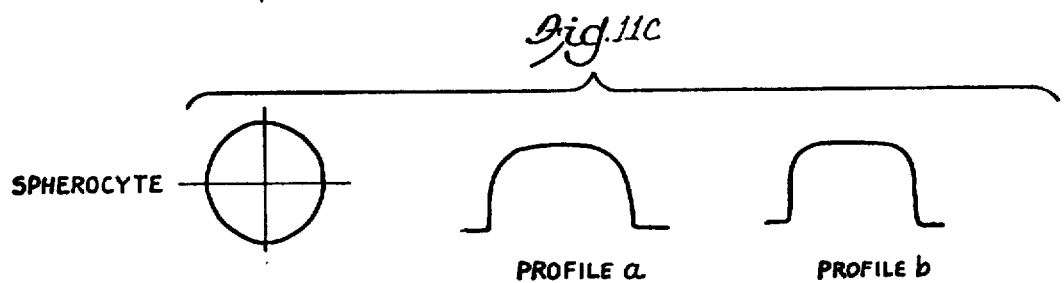
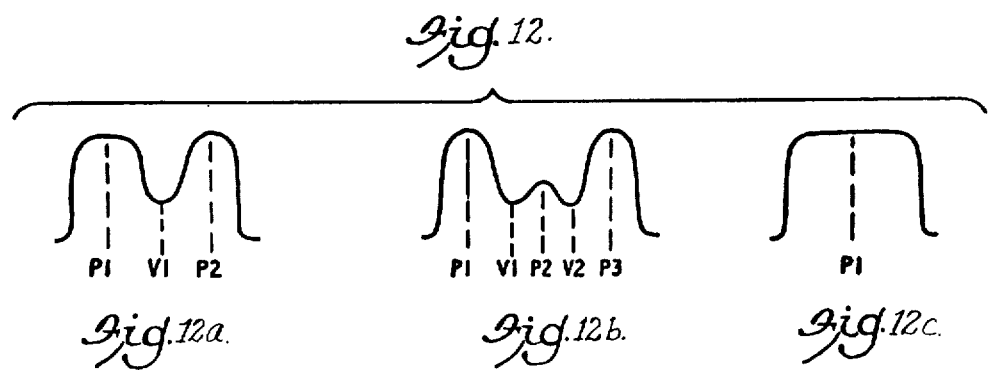

METHOD AND APPARATUS FOR MEASURING MEAN CELL VOLUME OF RED BLOOD CELLS

This invention is related to applicant's prior inventions disclosed in U.S. Pat. Nos. 4,097,845 and 4,199,748.

This invention relates to a method of and an apparatus for measuring and reporting size information about red blood cells and particularly the mean cell volume of red blood cells in a blood specimen.

In the prior applications referred to above, there is described various apparatus for automatically analyzing blood and providing representative output data of the mean cell size, mean cell hemoglobin, and mean cell density. The mean cell size information generated and reported was expressed as area ($u^2$) rather than volume ($u_3$) the latter being the conventional size information generated with conventional measuring techniques such as the Coulter kind of particle counting apparatus. Since physicians are most familiar with mean cell volume data than with mean cell area data, there is a desire to generate a mean cell volume output that can aid physicians and may also aid in automatic diagnosis of anemia or other blood disorders.

Some work has been done with image analysis and pattern recognition techniques to compare mean cell areas with mean cell volumes. Such equipment has not been very accurate in correlating with mean cell volume data generated by conventional Coulter particle sizing equipment used for blood analysis. The fault for this discrepancy may not be entirely with the image analysis equipment. As is known and has been reported in the literature, the Coulter blood counting equipment suffers from several shortcomings such as producing signals which are in error of a true blood cell volume for cells which are (1) tumbling as they pass through the measuring aperture, (2) passing very close to the aperture wall, (3) in reality a pair of closely adjacent cells in the aperture rather than a single cell, (4) being measured while a previously measured cell is closely adjacent the exit end of the aperture and is generating a ghost signal, etc.

The Coulter blood cell analyzing equipment is calibrated using spheres of a known size. However, the blood cells are flattened and thin and many red blood cells contain thin central areas called central pallors which reduce substantially the volume of the cell from the volume the cell would have if it did not have a central pallor. The change in size of central pallors of red blood cells appears to be a good indicator of changes in the blood disorders, as discussed in the first mentioned copending patent application. Hydrodynamic forces used in focusing the blood cells and passing the cells through the aperture of the Coulter cell sizing apparatus change the shape of the thin flexible cells from the shape the cells have in their natural relaxed state. To compensate for various ones of these factors, the Coulter counter is provided with a shape factor, so that the actual measured signal from the measuring aperture is multiplied by this factor to obtain the final value of mean cell volume. It is thought that this shape factor is about 1.4 for today's conventional Coulter equipment.

Another reason for preferring to generate mean cell volume data for red blood cells rather than mean cell area is a better segregation of the data into more meaningful and more discrete patterns for blood order diagnosis. More specifically, cells may be substantially similar in area and differ markedly in volume because of central pallor size or a lack of central pallor. For example, normal blood cells and iron deficiency cells each typically have sizes clustered in about the 40 to 60 square micron range and it is not possible to distinguish such cells from one another on the basis of area. However, these same normal cells should have volumes clustered in range of about 75 to 100 cubic microns which is substantially different than the range of about 50 to 75 cubic microns for the iron deficiency cells. A graphic illustration of the plot of mean cell area by an image analysis technique versus mean cell volume from a Coulter counter type of sizing apparatus is set forth in FIG. 1 of an article of "Bentley, S. A. and S. M. Lewis, 'The Use of an Image Analyzing Computer for the Quantification of Red Blood Morphological Characteristics', Brit. J. Haemat. 29:81, 1975". The cells used in this study were selected manually from each patient specimen and were processed with off-line general purpose computer equipment. Unlike the apparatus used in that work, a commerically practical image analysis system must be automatic, and competitive in speed and cost with the Coulter system in obtaining information on cells.

The Bentley and Lewis technique, the Wintrobe Indices technique, and the Coulter counter technique all provide size information for the total blood cell count and cannot make and correlate size data for a given kind of cell or for a given subpopulation of abnormal cells. With the equipment described in the copending applications, it is possible to segregate and to measure the size of individual cells as well as the mean size for various abnormal cell subpopulations such as spherocytes, macrocytes, microcytes, etc. However, as above explained, the area differentiations are not as separated as volume size characteristics. By providing mean cell volume for subpopulations of abnormal cells on a large scale basis, new insights should be gained into the cell volume characteristics of a given blood disorder and should lead to more substantial and more accurate information on the volume relationship of abnormal cells to normal cells. For example, very specific data as to volume differences for microcytic cells versus normal cells because of the difference in the thicknesses (the microcytic cells being thinner) as well as the differences in areas at various times from a patient undergoing treatment may provide an insight as to the effectiveness of the treatment at a very early stage.

The present invention may also be used to correlate the sizes of cells measured into different classes or categories such as microcytic, normocytic, or macrocytic with the cell size measurements obtained with conventional techniques. Heretofore, cell sizes have been measured and classified into these classes by image analysis techniques but the results have been poor and did not correlate sufficiently with the results from conventional equipment.

Accordingly, a general object of the invention is to provide a new and improved method and apparatus for measuring the size of red blood cells.

Another object of the invention is to provide a method of and an apparatus in using a central pallor analysis in the red blood cells having central pallor as part of the determination of the mean cell volume for a specimen of cells.

A further object of the invention is to determine the mean cell volume of a total population or of a particular subpopulation of red blood cells.

A further object of the invention is to provide an image analysis of red blood cells and to derive therefrom a size classification or size data which is correlated with data derived with conventional equipment.

These and other objects and advantages of the present invention will become apparent from the following detailed description taken in connection with the accompanied drawings in which.

Figure 7A:
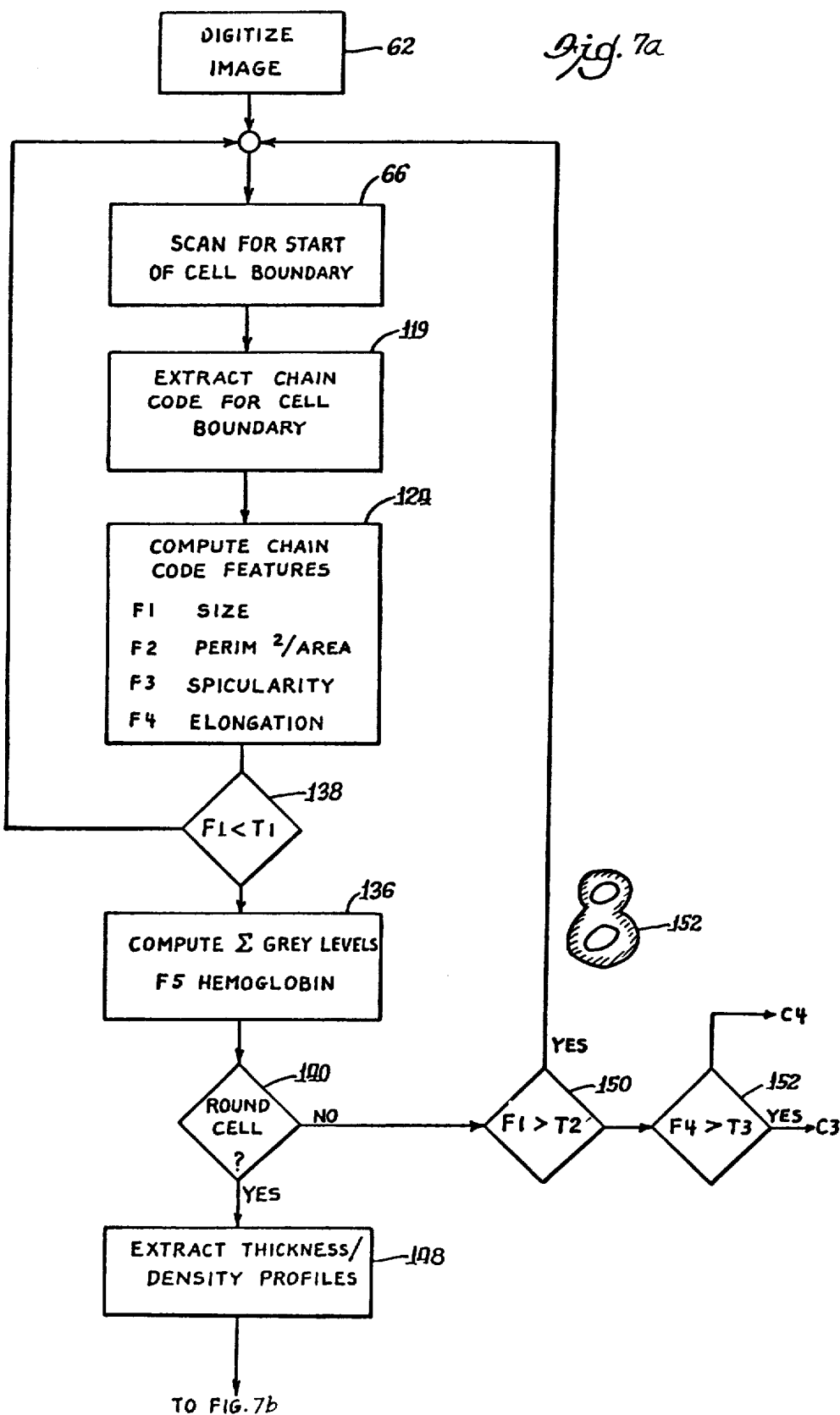
Figure 7C:
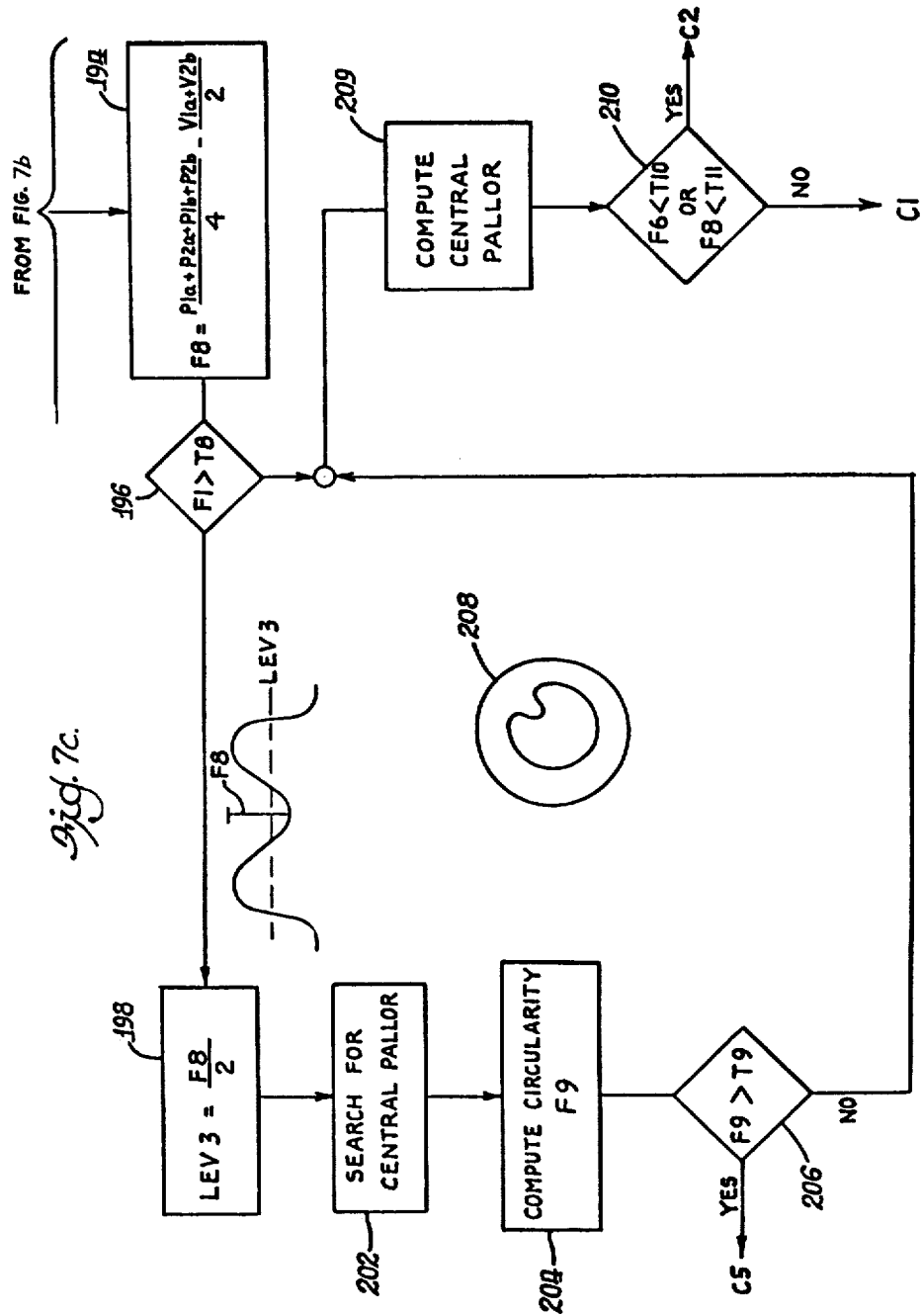

FIGS. 7a, 7b, and 7c are flow charts of the preferred techniques for classifying the blood cells into mutually exclusive subpopulations;

FIG. 8 is a diagrammatic view of a model for red blood cell central pallor measurement.

Figure 9:
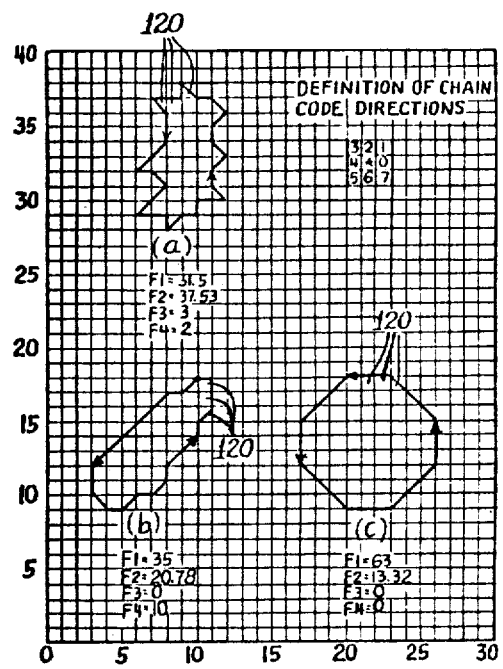
Figure 10:
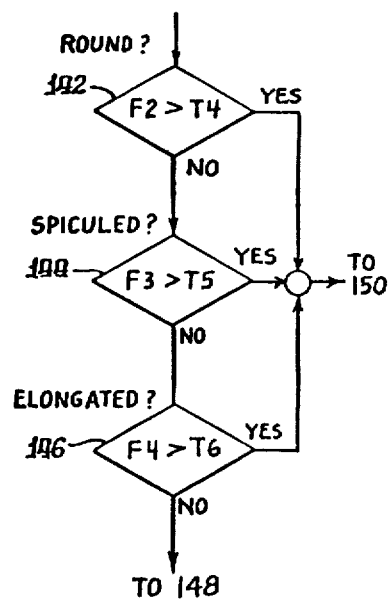
Figure 13:
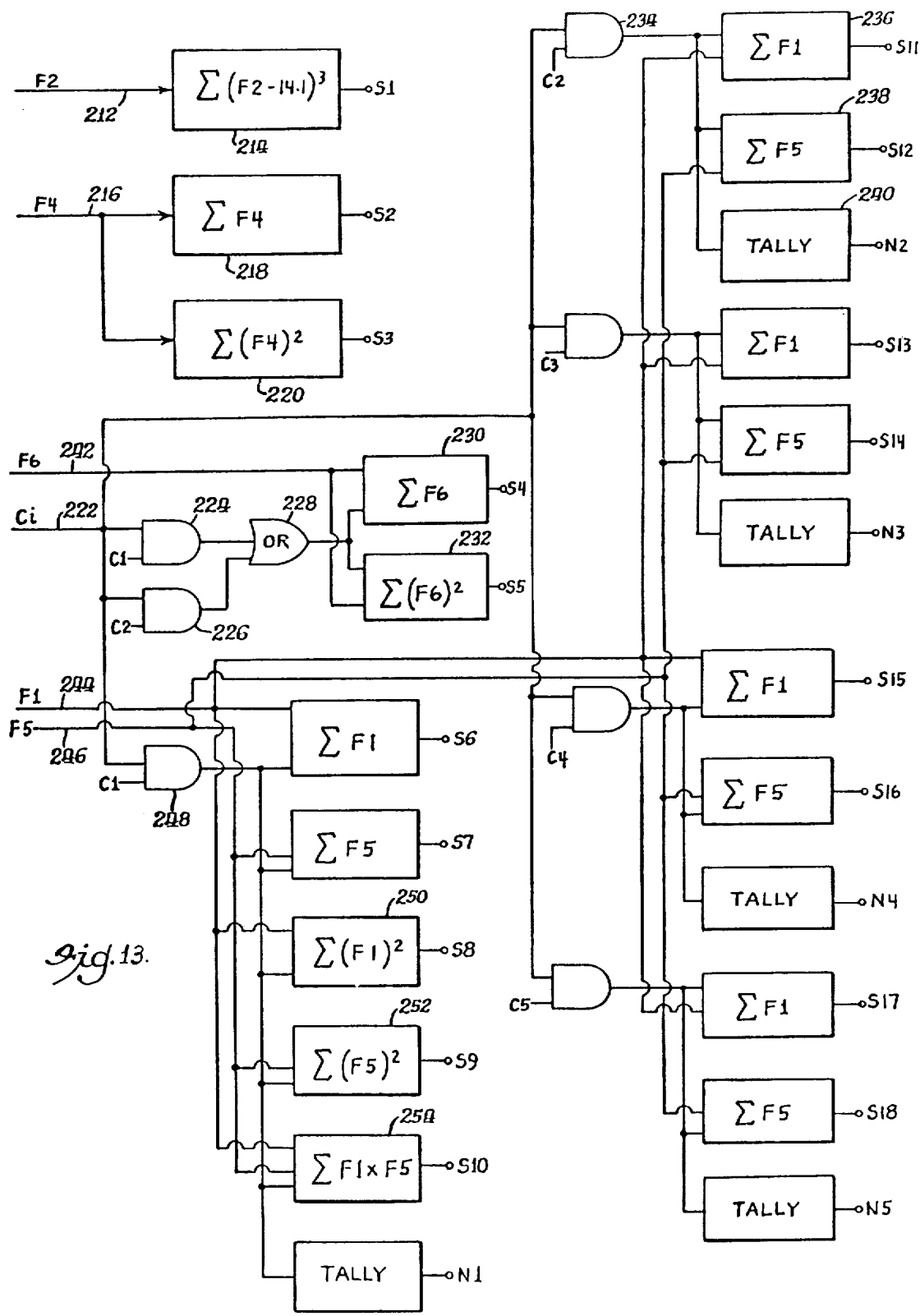

FIG. 9 illustrates a chain code description and analysis method for three diagrammatic red blood cell outlines;

FIG. 10 is a block diagram of the preferred process for determining whether a cell is round;

FIGS. 11a, 11b, and 11c are graphs illustrating thickness/density profile measurements for three different, typically appearing cell types, measured in two orthogonal directions. These profiles are used to measure the cell central pallor features and target cell features, FIG. 11c illustrating a "flat" cell having little or no central pallor development;

FIGS. 12a, 12b and 12c are graphs illustrating the profiles of the cells of FIGS. 11a, 11b, and 11c with the peaks and valleys of each profile labelled;

FIG. 13 is a schematic of the preferred process for accumulating red blood cell subpopulations parameters;

FIGS. 14a, 14b, 14c, 14d and 14e are schematics illustrating the preferred process of computing the subpopulation characteristics from the accumulated values from a plurality of cells; and FIG. 15 is a logic section for generating a mean cell volume report.

As shown in the drawings for purposes of illustration, the invention is embodied in an apparatus 10, such as disclosed in copending application Ser. No. 875,126 which application is incorporated by reference as if fully reproduced herein. In this equipment, as described fully in application Ser. No. 875,126, and as shown in FIGS. 3–6 herein the apparatus 10 comprises a microscopic digital image processing and pattern recognition system with analyzes a monolayer of red blood cells on a microscope slide 12 with the cells being spaced from each other to ease the automated classification thereof. Suitable high resolution microscope optics 14 form an optical image for each red blood cell on a vidicon television camera tube or other detector 16 which converts the scanned electronic charged distribution of the optical image point by point into a numerical or digitized image representing the optical transmission of the points in each image. The output of the vidicon camera is applied to digitizer electronics 20 which includes an analog to digital-converter which is connected to an image processing logic 22 which controls the digitizer electronics 20 and receives and stores the digitized cell images into a memory store. The image processing logic 22 operates on the digitized cell images in a manner that will be hereinafter described which includes cell feature extraction and cell classification.

A suitable stage motor means 24 is provided and controlled by stage motor electronic 26 which are in turn controlled by a master control logic 28. The stage motor 24 is provided to shift the slide 12 in order to iteratively process different image areas of the blood specimen on the slide. To control the focus of the microscope, a focus control motor means 30 is connected to the microscope and is operated by focus motor electronics 32 which are also controlled by the master control logic 28 by means of the focus parameter electronics 34. Focus control of slides for image analysis is well known in the art, e.g., U.S. Pat. No. 3,967,110.

Figure 3:
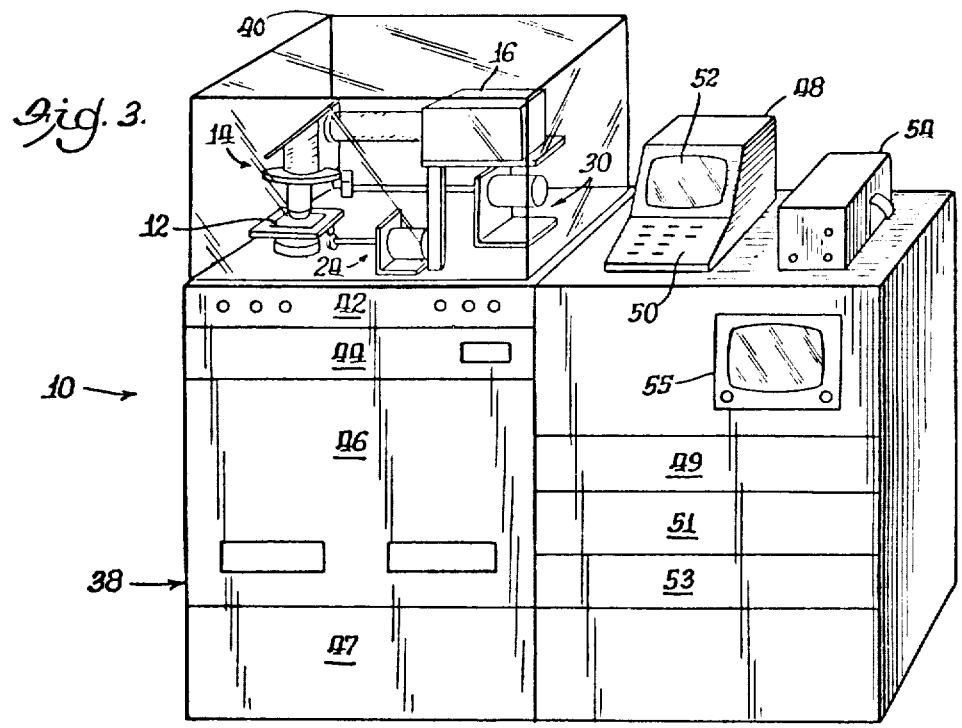
FIG. 3 is a perspective view of an apparatus for practicing the method and embodying novel features of the invention.

The apparatus 10 shown in FIG. 3 includes a housing 38 having a cover 40 enclosing the microscope optics 14 and the television vidicon 16. An upper section 42 of the housing 38 houses the control switches of the apparatus, the next lower section 44 houses the master control logic 28 with the next two lower portions 46 and 47 of the housing containing the memory store for the image processing logic 22 and master control logic 20 and the motor electronics 26 and 32. A terminal 48 is connected to the master control logic 28 and has a keyboard 50 for input of identifying information about the specimen or for other instructions. A monitoring screen 52 provides a visual display of the final report, and preferably a written printout is also made by a printer means 54 to afford a permanent record. A TV monitor 55 provides desired pictorial displays. The TV camera electronics are housed in a section 49 below the monitor. The next lower section 51 houses the analog to digital converter with the first section 53 housing the image processing logic 22. The results of the red cell analysis may also be transmitted for storage in a medical computer data bank.

Red blood cells may be examined such that normal cells are distinguished from abnormal cells and classified by the apparatus 10 into subpopulations automatically in a detailed fashion heretofore not possible by a manual/visual examination of cells. Also, each of the red blood cells being examined may be classified into mutually exclusive subpopulations and reported out so that the presence of a minor number of abnormal cells is not overlooked or forgotten and so that accurate parameters about a given subpopulation may also be provided. The individual red blood cells may be examined individually for the hemoglobin contents. Thus, a report may be made not only of the kind of cells found in the subpopulation but also of their number and their hemoglobin characteristics. Advantageously, the individual red blood cells may be analyzed and classified with less subjectivity into a large number of mutually exclusive subpopulations such as biconcave (round cells with central pallor), elongated cells, targets, and irregular cells (cells not fitting into any of the above classifications).

The preferred hemoglobin characteristic gathered from the analysis of the hemoglobin contents of the individual cells within a given subpopulation and reported out is the mean cell hemoglobin (MCH) for a given subpopulation of cells, such as shown in Table I of the aforesaid patent application. In addition to the hemoglobin parameters, the individual cells are counted for each subpopulation to provide their respective percentages of the total population; and likewise mean cell volume (MCV) for each subpopulation may also be reported out in a format such as shown in Table I in the copending application. It has been found to be helpful in detecting abnormalities in blood samples to determine multivariate distributions of the red blood cells in particular subpopulations of a sample with respect to a plurality of quantifiable features.

According to the method described in Ser. No. 875,126, red cell size was measured as the projected area of the red cell in square microns. This is a two-dimensional description of size and does not contain any volumetric information regarding size, such as the thickness of the cell, or a decrease in the volume of the cell due to increased central pallor. It was not evident prior to the invention that a projected area measurement of "size" in square microns, was not equivalent in a diagnostic sense to a volume measurement of "size" in cubic microns, such as that which could be obtained with a Coulter counter or the like, or by determining the hematocrit value of the blood sample and then dividing by the red cell count.

Figure 1:
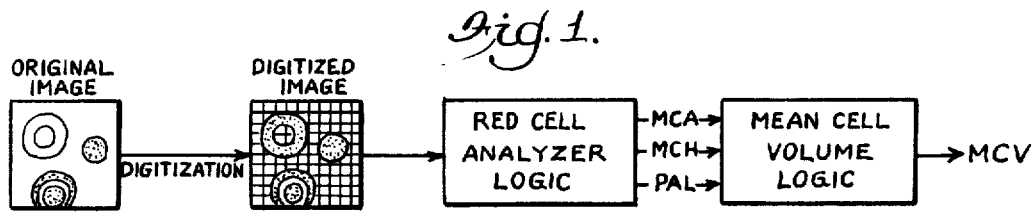
FIG. 1 is a block diagram of the preferred embodiment of the invention.
Figure 2:
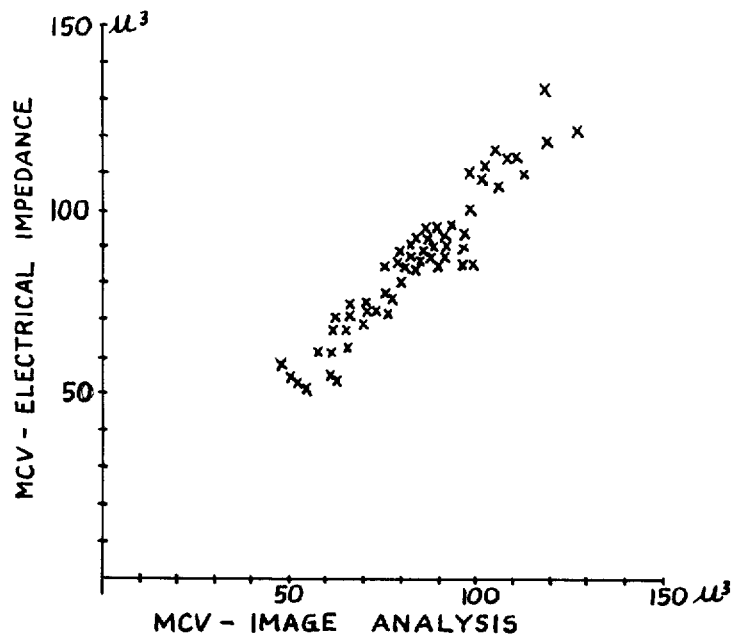
FIG. 2 is a graph illustrating the mean cell volume data as generated by the present invention and by conventional equipment.
Figure 2A:
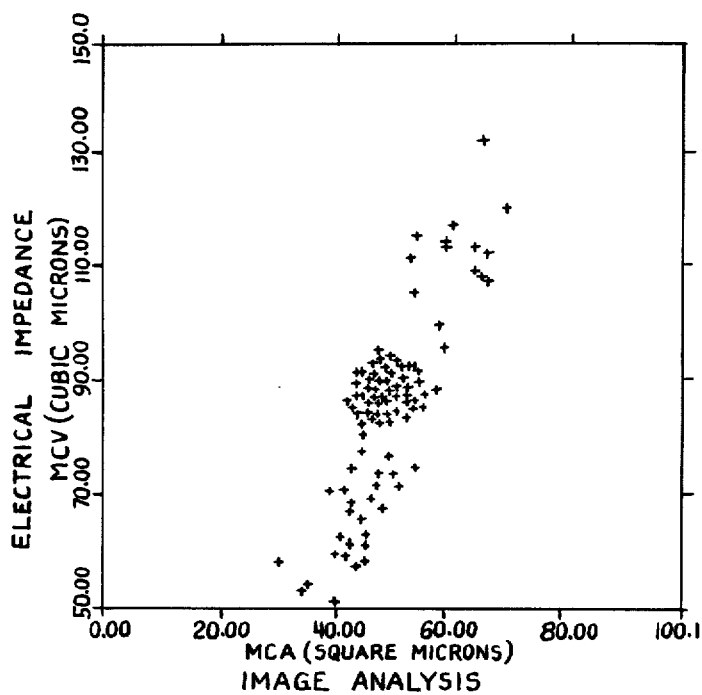
FIG. 2A is a graph illustrating a comparison of mean cell area and mean cell volume for the same blood specimens indicated in FIG. 2A.

Experimentation with normal and several types of anemic blood specimens have recently indicated that the diagnostic information relative to size is better preserved as a volume measurement rather than an area measurement. This can be better understood from FIG. 2A, in which are compared cell size measurements from the blood of persons with iron deficiency anemia, megaloblastic anemia and normal blood. Size measured by an electrical impedance apparatus, in this case the Coulter Model S (MCV) is compared to the area analysis (MCA) from the image analysis equipment disclosed in the aforesaid co-pending application. Notice that if the results are projected on the MCV axis there are three distinct clusters, i.e. a separation of data; whereas, if the results are projected on the MCA axis these distinctions are not as apparent. This indicates that an inclusion of volumetric information is desirable when reporting a measure of red cell size.

In accordance with the present invention, mean cell volumes are generated which take into account the central pallors of the red blood cells to provide data which may be directly correlated with MCV data generated in the past or presently being generated by conventional equipment using conventional Coulter counter equipment. This is achieved by using central pallor data or central pallor signals in combination with the area and hemoglobin characteristic data or signals to generate an output representative of the mean cell volume which takes into consideration the actual volumes of the individual central pallors (if any) of the cells being measured. As diagramatically illustrated in FIG. 15, representative signals of mean cell area (MCA), mean cell hemoglobin (MCH), and mean cell pallor (PAL) are generated with the above described apparatus and are sent to a means which generates an output representative of the mean cell volumes for the blood cells. The accuracy of the present invention to providing mean cell volume as related to similar measurements from a Coulter counter instrument is readily apparent from a consideration of FIG. 2. The data from the image analysis is substantially similar on the ordinate for the volume on the abscissa for the Coulter counter measurements of the same blood samples.

To achieve this MCV measurement, four parameters $K_1$, $K_2$, $K_3$ and $K_4$ are used in connection with the measured values of MCA, MCH and PAL, with the parameters $K_1$, $K_2$ and $K_3$ each being a multiplier for these measured values as indicated in FIG. 15. The values for $K_1$, $K_2$ and $K_3$ have been determined experimentally as will be explained hereinafter. A fourth factor $K_4$ is added to the sum of $MCA(K_1) + MCH(K_2) + PAL(-K_3)$ and is an offset factor indicating the amount of offset from the juncture of the abscissa and ordinate of a plot of the MCV's. This offset is through to represent a factor due to drying of the blood cells prior to image analysis with the apparatus 10 disclosed herein. As will be explained, in the described embodiment of the invention, these values are $K_1 = 0.43$; $K_2 = 1.94$; $K_3 = -0.84$ and $K_4 = 27$. The preferred means for determining mean cell volume comprises either a digital logic system of electrical devices or a programmed microprocessor which uses Boolean logic.

In the analysis given in aforesaid copending application, the cells are classified into subpopulations related to a specific anemia such as set forth in Table I therein. In U.S. Pat. No. 4,097,845, the subpopulations given in Table I were into hematologically recognized subpopulations such as normocytes with central pallor, normocytes without central pallor, spherocytes, etc. with the size of the cells being listed as mean cell area in square microns. In this same patent several examples were printed out. Manifestly, the mean cell size may be printed out for the entire population as well as for a given subpopulation. Likewise, with only slight modification of the analysis logic described herein the mean cell volumes given hereinafter may also be given for subpopulations as well as for the total population.

To aid in understanding classification of the cells as well as the measurements used to classify the cells prior to determining the mean cell volumes therefor, some of the description given in the aforesaid copending patent application will be repeated. As will be explained, the present invention is capable of reporting the total population and the average mean cell hemoglobin as well as the average mean cell volume for the entire population, the average mean cell hemoglobin may be reported out in the line with average parameters of Table I of the aforesaid copending application. Thus, as indicated above, herein the invention will be described as having the ability to classify red blood cells into the several mutually exclusive subpopulations set forth in Table I of the aforesaid application. The subpopulations listed therein are preferred subpopulations for classifying blood with respect to recognized categories of anemias but there may be other subpopulations defined. It is also possible to provide a mean cell hemoglobin for a subpopulation of cells, such as biconcave cells, as will be explained hereinafter. Addtionally, it is possible with modifications of the analysis logic to determine the cell volume for each cell and then to subsequently determine the mean cell volume for the total population or for any given subpopulation of course, the size classification of the cells may be reported out in other manners such as microcytic, normocytic, or macrocytic.

The present invention is also of utility in correlating other and existing equipment which has not performed adequately in reporting out cell size classifications as microcytic, nomocytic, or macrocytic for the reason that the reported classfication did not match the results obtained with conventional equipment.

Figure 4:
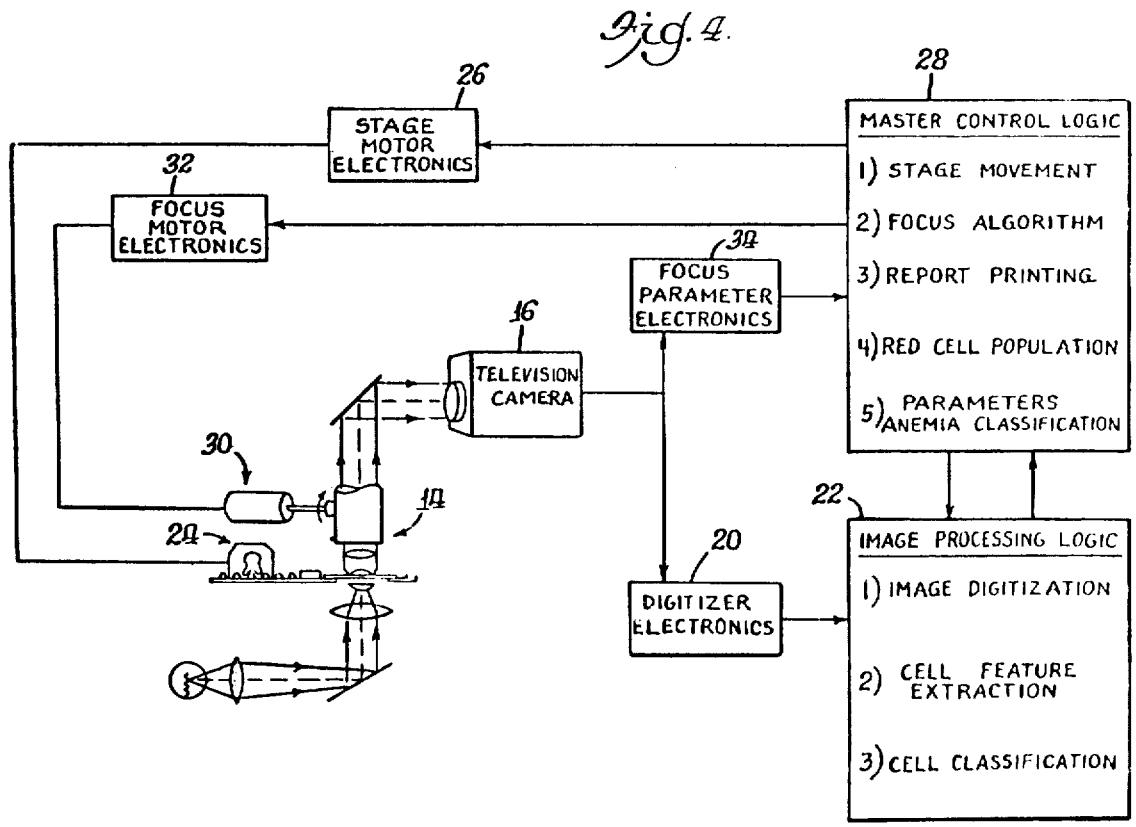
FIG. 4 is a block diagram showing the operation of the apparatus illustrated in FIG. 3.

As disclosed in the aforesaid copending application, a multiple parallel logic architecture has been found to provide the rapid processing necessary for efficient analyzing of cells on a slide. Herein, there is provided a first processing means, the master control logic 28 (FIG. 4), and a second processing means, the image processing logic 22 as shown in FIG. 4. The analysis of the cells on a slide requires a sequence of operations to be performed, and since one operation often requires the results of a previous operation, there are provided synchronizing means for synchronizing the processors so that the results necessary to perform a particular operation are available when that operation is begun.

Figure 5:
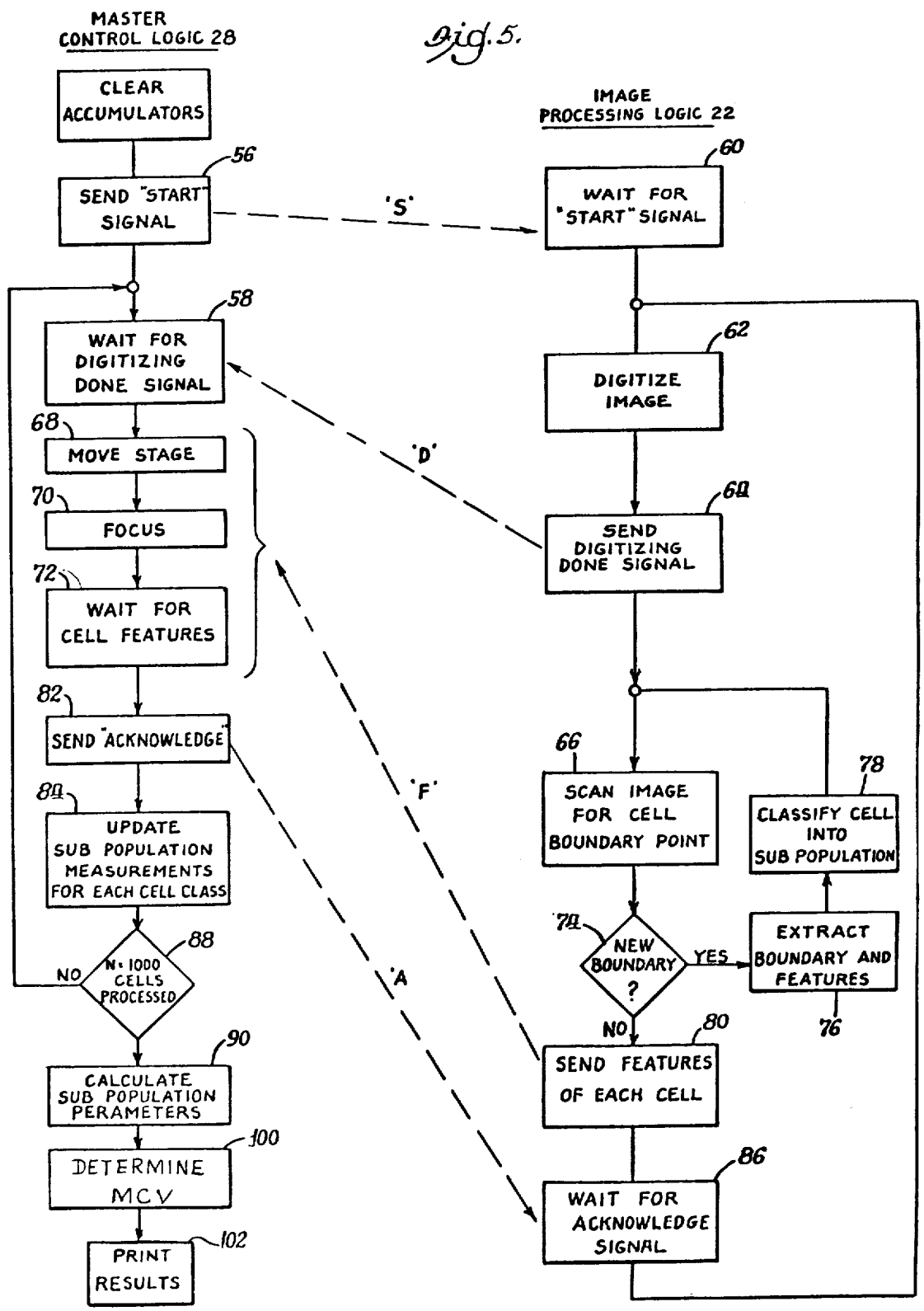
FIG. 5 is a block diagram of the preferred process for analyzing and classifying blood cells and for determining mean cell of volumes.

FIG. 5 illustrates the specific interrelationships between the master control logic 28 and the image processing logic 22. Because of this multiple parallel logic or architecture, the master control logic may proceed with one task or operation while the image processing logic is proceeding with another operation.

As seen in FIG. 5, the operations carried out by the master control logic 28 are listed in the lefthand column with the operations of the image processing logic 22 in the righthand column. The master control logic, after clearing its associated accumulators, proceeds to operation 56 in which a start signal is sent to the image processing logic and thereafter continues to operation 58. The image processing logic meanwhile is waiting for the start signal (operation 60) from the master control logic. Upon receipt of the start signal, the image processing logic 22 proceeds to operation 62 which includes digitizing the image produced by the vidicon camera 16 (FIG. 4). Upon completion of the digitizing, the image processing logic sends a "digitizing done" signal (operation 64) to the master control logic indicating the completion of the digitizing process and proceeds to operation 66. The master control logic operation 58 is currently waiting for the "digitizing done" signal and upon its receipt proceeds to move the stage (operation 60) on which the slide rests so that a new field of cells may be imaged since the previous field has already been digitized by the image processing logic 22. The optics 14, FIG. 4, are providing an imaging means of the cells on the slide. The stage motor drive 24, and the focus motor drive 30, and their associated electronics, are controlled by the master control logic 28. After moving the stage so that a new field may be imaged, the master control logic proceeds to operation 70 wherein the field is focused and then proceeds to operation 72.

After transmitting the "digitizing done" signal, the image processing logic scans the digitized image for a cell boundary point (operation 66). If a cell boundary point is found (operation 74), the image processing logic extracts the cell's boundary and features (operation 76) and classifies the cell as to its proper subpopulation (operation 78).

The image processing logic then returns to operation 66 and continues scanning the image for another cell boundary point. The scanning, feature extraction, and cell classification operations will be described in more detail below. If the logic section 74 determines that a new boundary point has not been located, then the image processing logic proceeds to operation 80 wherein the features of each cell located as well as each cell's subpopulation classification is transmitted to the master control logic which will be in the process of executing operations 68, 70, or 72. The transmittal of the information is on an interrupt basis, i.e., should the master control logic be in the process of controlling the imaging means (operations 68 or 70), the master control logic will interrupt these operations and store the information received from the image processing logic before proceeding with moving the stage and focusing the microscope. However, if these operations have already been completed then the master control logic proceeds to operation 72 wherein the master control logic waits for the data to be transmitted from the image processing logic. In response to the receipt of the data, the master control logic will transmit an acknowledge signal (operation 82) to the image processing logic and then proceeds to operation 84 wherein the subpopulation data for each subpopulation is updated, as will be more fully explained below.

Upon receipt of the acknowledge signal, the image processing logic proceeds to digitize the image of the new field that has been moved into view by the master control logic. The master control logic, upon completing the update of the subpopulation data, determines at logic section 88 whether N, the total number of cells processed, is equal to 1000. If 1000 cells have not been processed, the master control logic returns to operation 58 and waits for the "digitizing done" signal from the image processing logic, otherwise the master control logic calculates the subpopulation parameters (operation 90) proceeds with a means cell volume (MCV) determination (operation 100) and prints the results (operation 102), as will also be more fully explained below. The apparatus may be used to provide an output of an anemia classification as described in the aforementioned copending applications, or the present invention could be made a "stand alone" unit whose only function would be to provide mean cell size (MCV) for a total specimen without having to do any classifying into subpopulations, or anemia classifications.

Thus, because of the dual processor architecture, the master control logic is free to control the imaging means wherein a new field is brought into view to be imaged while the image processing logic is proceeding with the digitizing and analyzing of the image from the previous field. Similarly, while the master control logic is accumlating the data extracted from the image by the image processing logic, the image processing logic may simultaneously digitize and analyze a new image provided by the new field which had been brought into view by the master control logic. It should be noted that although for purposes of illustration only one image processing logic is described as associated with the master control logic, it is capable of utilizing information from several image processing logics operating in parallel and independently on different images.

With the present invention, the optimization of the time of analysis as well as the number of features used in the classification logic is achieved so that the amount of storage and classifying techniques may be reduced substantially along with equipment requirements therefor. With an optimization of analysis time for classification, there is a danger that the reliability and accuracy of the classification are compromised. Despite this, a relatively foolproof feature set and classification logic has been invented for a large number of subpopulations such as those shown in Table I in the aforesaid application. The preferred classification features are size, hemoglobin content, spicularity, roundness, elongation, central peak height (if present) from cross-sectional cell scans, and central pallor. By suitable combinations and analyses of such features, it is possible to differentiate from normal blood and to identify biconcave round cells, spherocytes, target cells, irregular-shaped cells, and elongated cells.

In the preferred method and apparatus, the cell classifications are achieved by an image processing and pattern recognition with great accuracy and reliability by rendering white blood cells and other artifacts substantially invisible to the optics 14 by using a light having an optical wave length of about 415 Nanometers. At this optical wave length, the red blood cells and other formed elements are substantially invisible. The staining of the red blood cells prior to being analyzed by a microscopic image processing technique has been found to be a time-consuming process, as well as undesirable in that the staining may introduce a number of stained artifacts which detract from the accuracy of the analysis. Furthermore, many of the stains are not stoichiometric in the representation of hemoglobin concentration according to density, thus distorting the quantization of the hemoglobin content of the cell on a per-cell basis. A particular manner of vapor fixing of cells before they dry without staining thereof to prevent the formation of artifacts by distortion of the central pallor is disclosed in my co-pending application entitled "Method and Apparatus for the Preparation of Blood Samples for Automated Analysis", now U.S. Pat. No. 4,209,548 filed Dec. 21, 1977, and hereby incorporated by reference as fully reproduced herein. Thus, by rapidly preparing the specimens to a monolayer and fixing with a formaldehyde vapor prior to the drying of red blood cells, as disclosed in the aforementioned co-pending patent application, and by not employing a time consuming staining to contrast enhance the cells, as in white blood cell analysis, these specimens may be quickly prepared and analyzed accurately.

The location of the cell image and the identification and feature extraction has been greatly simplified as described below to locate and define the cells by a boundary procedure which defines the cell in the form of an octal chain code. The use of octal chain codes as an image processing technique is described in a paper by H. Freeman, "Computer Processing of Line-Drawing Images", ACM Computing Surveys 6:57, 1974. As will be explained in greater detail, the octal chain code allows feature extraction as to: (1) cell size, (2) perimeter length and roundness shape measure, (3) irregular shape measure, and (4) elongation shape measure. This is followed by extracting the summed density or hemoglobin feature, and then by extracting cross-sectional scans (thickness/density profiles) for central pallor measurement and target cell measurement. Finally, inner central pallor boundaries are determined and features analyzed for more precise target cell identification.

After having extracted these identifying features, the cells are then categorized by a classification means. The preferred classification means (FIGS. 7a, 7b, and 7c) comprise either a digital logic system of electrical devices or a programmed microprocessor which uses Boolean logic to classify the red blood cells.

Referring now in greater detail to the specific features of the illustrated embodiment of the invention, the images of the cells are digitized (operation 62 of FIG. 5) in a manner known to the art, e.g., U.S. Pat. No. 3,883,852 as a television digitizing system. Magnified blood cell images are obtained by using microscope optics with ultraviolet illumination, arranged to provide a 0.23 pixel resolution in the image plane. A pixel is a picture element having a specific location in the digitized image stored in the memory analyzer.

Figure 6:
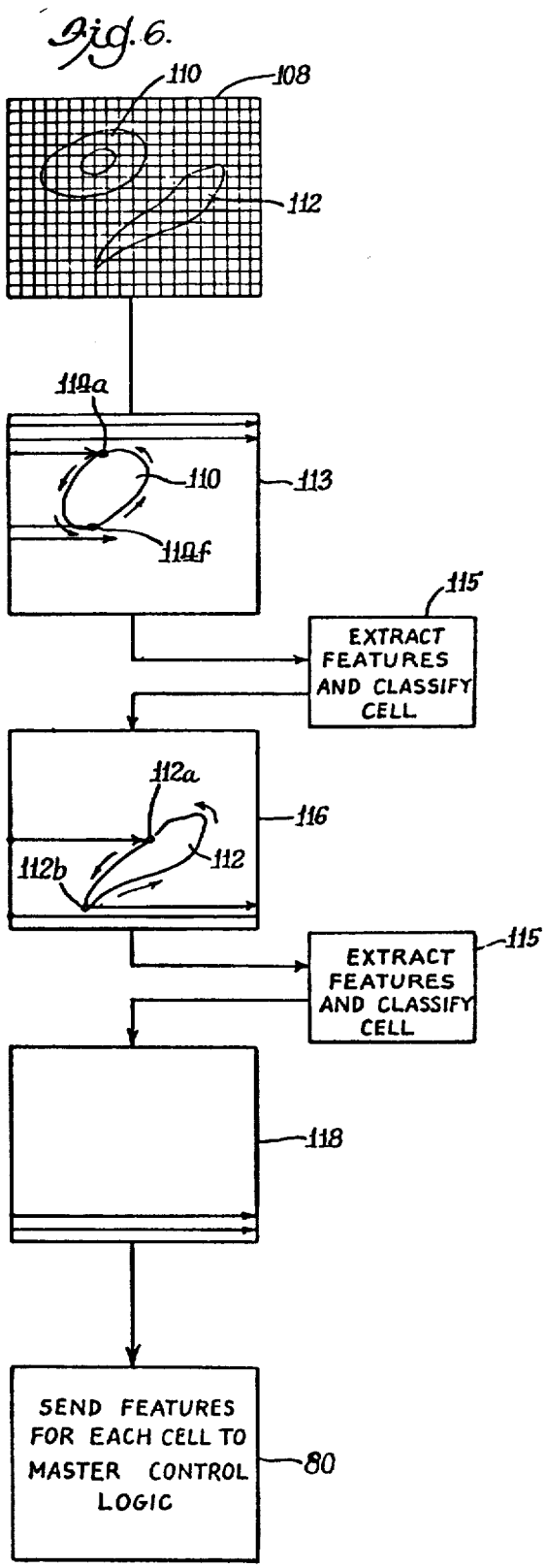
FIG. 6 illustrates a scanning technique for locating cells and determining the boundary points of cells in an image.

Referring now to FIG. 6 which illustrates in greater detail the operation 66 (FIG. 5) by the image processing logic, an original microscopic image which had been digitized is stored as represented by the image 108 for the purpose of further analysis. This analysis is carried out by the image processing logic and is represented by the blocks indicated at 115 which comprise the operations 76 and 78 (FIG. 5). In this preferred embodiment of the invention, individual cells 110 and 112 in a digitized image 108 are located by a technique in which a raster scan is made of the digitized image to locate objects above a critical threshold, such as illustrated for cell 110 in block 113. The boundary of the cell is traced by examining the neighboring pixel elements by a counterclockwise search, by techniques which are well known in the art. One such technique is disclosed in U.S. Pat. No. 3,315,229. During this counterclockwise boundary tracing operation herein, the picture element at the "top" of the cell, pixel 114a, which is usually the pixel located first, and the one at the "bottom" of the cell, here pixel 114f, are stored for reference in the later analysis. The analysis process then proceeds to extract features and to classify the located cell into one of a plurality of subpopulations, as in block 115, and as described in detail later.

The raster scan of the digitized image is then continued from the bottom pixel 114f to hit the next digitized cell 112 by impacting a pixel 112a which is above the threshold as seen in block 116. After the boundary is traced and the features for this cell are extracted and the cell is classified, the raster scan continues from the bottom pixel 112b, and, as seen in block 118, no more cells are located in the image field. At this time, the image processing logic transmits the cell features and subpopulation classifications to the master control logic (operation 80) as shown in FIG. 5.

The initial image processing done by the image processing logic outlined in FIG. 5 is shown in greater detail in FIG. 7a. After the image has been digitized (operation 62), the image is scanned to locate a cell (operation 66) and the boundary is traced as explained above.

During this boundary tracing operation, octal chain codes are formed in an operation 119. The outer boundaries, defining a cell, are processed in the following manner. Each pixel element defining the boundary is stored in a list as a series of numbers indicating a line description of the cell. For instance, referring to FIG. 9, a digital image of cells as defined by their boundary pixels 120 are illustrated.

As is well known in the art, e.g., as described in "Bacus, J. W. and J. H. Weens, 'An Automated Method of Diffential Red Blood Cell Classification with Application to the Diagnosis of Anemia', Journal of Histochemistry and Cytochemistry, 25:7, 1977", a plurality of features F1–F4 can be computed from this chain code. The details of this computation are fully described in the aforementioned publication, which is hereby incorporated by reference as if fully reproduced herein.

The above features are combined with other features for use in the classification of the cells. In this regard, the following features are used herein:

TABLE II

| Feature | Description | How Determined |
|---------|-------------|----------------|
| F1 | Area size | Number of pixels enclosed by cell boundary |
| F2 | Shape (circularity) | (Number of perimeter pixels)$^2$/area |
| F3 | Shape (spicularity) | Number of "spicules" on boundary |
| F4 | Shape (elongation) | Comparison of orthogonal boundary chain code orientations |
| F5 | Grey levels | Sum of grey levels as a measure of Cell Hemoglobin |
| F6 | Pallor (volume) | The percentage volume of the central pallor |
| F7 | Central peak | The height of the central peak of a 3-peaked profile of a cell |
| F8 | Pallor (depth) | For a 2-peaked profile, the difference of the valley from the peak heights |
| F9 | Pallor (circularity) | (Number of pallor boundary pixels)$^2$/area of pallor |

As indicated above, features F1–F4 are calculated in an operation 124 by the image processing logic as shown in FIG. 7a. Feature F1 relates to the area or size of the cell as determined by the number of picture elements or pixels that are enclosed by the cell boundary. Feature F2 is the (boundary perimeter)$^2$/area and is of assistance in classifying round and non-round objects. A round object would have a theoretical value of 4 and non-round objects have greater values.

In actual practice the value of the perimeter squared divided by the area for round digitized objects varies as a function of the number of pixels, and in addition always involves quantization error, such that in practice for quantized circles the value approximated is 14.0, and is a better approximation to this reference number as the number of pixels, or size, of an object increases.

Features F3 and F4 relate to the spicularity and elongated shapes, respectively, F3 being a count of the number of spicules in a chain code boundary, and F4 measuring the non-roundness due to elongation of the boundary, as shown in FIG. 9. Feature F5 is the integrated optical density of the cell (operation 136). It is the sum of the grey levels within the enclosed boundaries of the cell. Feature F6, which is a measure of the pallor volume, assists in distinguishing cells with large pallors, such as hypochromic cells from normocytes. Feature F7 is equal to the larger of the two central peaks of two cross-sectional orthogonal 3-peaked thickness/density profiles, either having central peak, and is used to detect target cells. Feature F8 is a measure of the depth of the central pallor, as determined from two cross-sectional, orthogonal, 2-peaked thickness/density profiles. Feature F9 is a measure of the degree of roundness of the pallor itself, and is also used in distinguishing target cells.

The logic decisions for determining the various features that have been briefly described are carried out by the image processing logic using the logic flow chart shown in FIGS. 7a, 7b, and 7c. The logic decision are made using the various features together with threshold values that are identified as T1 through T11. The thresholds T1–T11 are described in Table V and specific values are also provided. As shown therein, the thresholds are used by the logic with the various features in making logic decisions leading to the classification of the cell of interest in accordance with the flow chart shown in FIGS. 7a, 7b, and 7c. In this regard, FIGS. 7a, 7b, and 7c illustrate various decisions that are made on the basis of various features either exceeding or being less than certain threshold values as will be specifically described.

Referring to FIG. 7a, an object that is located is examined by logic section 138 to determine if it is sufficiently large to be a cell, rather than a noise or dirt artifact, and thus is to be further analyzed. If feature F1, which is the size or area of the object under consideration, is less than the threshold value T1 which may be a value of about 6 microns$^2$, then the object is not considered by the decision logic and another object will be located for analysis and classification. However, if the area of the cell is greater than the threshold value T1, feature F5 is computed in operation 136 wherein the hemoglobin content of the cell is determined. This is simply a summing of the grey levels inside the boundary of the chain coded cell and then dividing by a conversion factor 1290 or thereabout to convert the grey level measurements to picograms of hemoglobin per cell.

For this purpose the electronics generating the television signal and digitizing said signal should be adjusted to produce grey levels corresponding to the following optical density at 418 nanometers:

TABLE III

| Optical Density | Grey Level |
|-----------------|------------|
| .134 | 17 |
| .294 | 35 |
| .403 | 52 |
| .505 | 43 |
| .605 | 57 |

Also, for calculation of hemoglobin and the area, the optics and television electronics should be adjusted such that round objects of the following dimensions produce the given number of pixels.

TABLE IV

| Size 2 | Pixels |
|--------|--------|
| 111 | 1850 |
| 93 | 1550 |
| 77 | 1283 |
| 58 | 967 |
| 34 | 567 |
| 23 | 383 |
| 17 | 283 |
| 4 | 67 |

The decision logic then operates to determine whether the cell is round or non-round. This is performed by a logic section indicated generally 140. the logic section 140 is shown in FIG. 10 to include logic subsections 142, 144, and 146. The subsections 142, 144, and 146 are operable to jointly make the roundness determination with the features F2, F3, and F4 being examined with respect to thresholds T4, T5, and T6. If the cell has a small roundness value, a small spiculated value, and a small elongated value, then it is considered to be round and is passed on to the next operation 148 (FIG. 7a) which is the first step in the target cell analysis and central pallor analysis. Similarly, if it is determined that the cell is not round, then logic subsection 150 (FIG. 7a) operates to determine if the size of the cell exceeds an upper boundary threshold T2, and if it does, the cell is not further analyzed and a new cell will be considered. The effect of the subsection 150 is to eliminate double cells such as that shown in the pictorial representation 152. It should be appreciated from the pictorial representation that such a double cell would not pass the roundness test, but it is also not a nonround cell of the type for cells of classes 3 and 4. Thus, it cannot be accurately classified and it is for this reason that the subsection 150 eliminates such cells from further consideration.

As previously mentioned, the roundness of the cell is determined by feature F2 which will have a value of 14.0 for a perfect circle and will increase as the shape of the cell departs from circular. Thus, the threshold value T4 is chosen to reflect reasonably good circularity and if the feature F2 exceeds the threshold T4, that is an indication that the shape is not circular, hence the logical flow to subsection 150 indicating that the object is not round. If feature F2 is not greater than threshold T2, it is one indication that the cell is round and if the decision from the subsections 144 and 146 also indicate adequate roundness, the logic flow then proceeds to logic subsection 148 (FIG. 7a).

In operation 148 thickness/density profiles are extracted from the cell image. These profiles are illustrated in FIGS. 11a–11c and 12a–12c. A thickness density profile is determined by the grey levels of the pixels along a particular direction across the cell image. As noted earlier, the grey level of a pixel is determined by the hemoglobin density at that point. It has been found that the grey level of the cell at a particular point is related to the hemoglobin density and the cell thickness at that point. Two such thickness/density profiles, profile a and profile b, are shown in FIG. 11a for a biconcave cell determined in two orthogonal or transverse directions, a and b. Two profiles each are also illustrated in FIGS. 11b and 11c for a target cell and a spherocyte cell. As seen in FIG. 11b, one direction (direction a) practically missed the center area. Since these profiles are used to distinguish target cells (feature F7), two transverse directions are preferably analyzed. Thus for each cell, two cross-sectional profiles are determined wherein the profile relates to the thickness of the cell along the points of the cross sections.

A profile for each cell of FIG. 11 is discussed more fully in connection with FIGS. 12a–12c. As seen in FIG. 12a, the profile has two "peaks", P1 and P2, and one "valley", V1. P1 and P2 are relative maxima of the profile of the cell with respect to the cell thickness and thus determine the two relative maximum thickness density points along the profile. V1 determines the relative minimum point of thickness density. Similarly, the target cells have three relative maxima, P1, P2, and P3, with two relative minima, V1 and V2, as shown in FIG. 12b. The spherocyte has one peak, P1, and no valleys (FIG. 12c). These profiles are utilized in a target cell analysis and a central pallor analysis as will be more fully explained hereinafter.

After the image processing logic extracts the thickness/density profiles for the cell, it proceeds to the target cell analysis performed by the logic section, referred to generally at 156 of FIG. 7b. The first step of the target cell analysis is to smooth the two profiles, profile a and profile b, as shown in operations 156 and 158, which is performed by the image processing logic before proceeding to a logic subsection 160. The logic subsection 160 determines whether a profile has three peaks and if so forwards it to an operation 162 which determines half the average of the two non-center peaks, P1 and P3, or "LEV1". A logic subsection 164 determines whether the two valleys, V1a and V2a, are less then LEV1 and if so then the cell located might be a target cell and the image processing logic proceeds to examine profile b. If not, then the valleys are not deep enough in profile a to be a target cell, so the center peak, P2a, is set to zero in an operation 166 and profile a is smoothed to two peaks or less in an operation 168.

After profile a is examined, profile b is examined for three peaks in a logic subsection 170. If the logic subsection determines that profile b has three peaks, it is forwarded to an operation 172 and logic subsection 174 wherein the two valleys, V2a and V2b, are compared to LEV2 which is half the average of the two non-center peaks P1b and P3b as for profile a. If the two valleys are less than LEV2, then it is forwarded to operation 176 wherein the feature F7 is determined as to which is the larger of the two center peaks, P2a and P2b, of the profiles a and b. Feature F7 is compared to a threshold T7 in a logic subsection 178, and if larger, the cell is classified as a target cell (C5). In other words, if the larger of the two center peaks is larger than a certain threshold, then the cell is determined to be a target cell. If not, then the center peaks of the profiles are probably due to "noise" in the image video and digitizing and not due to a center area of a target cell. In that case, both profiles are smoothed to two peaks or less in operations 180 and 183. However, if the logic subsection 174 determined that the valleys of profile b were not less than LEV2, then the profile b is forwarded to a logic subsection 184 which checks whether the center peak of profile a had been set to zero. If not, then profile a may have detected a target cell and thus P2b is set to zero and subsection 176 determines the maximum value for F7 as described.

If the center peak, P2a, had been set to zero, then neither profile has passed the tests at logic subsection 164 and 174 respectively. Thus the cell is probably not a target cell and profile b is also smoothed to two peaks or less at operation 182. However, some target cells might not be detected in this analysis, therefore, other tests are performed on the cell as will be explained later.

After the center peaks of profiles a and b have been examined as explained above, a logic subsection 186 determines whether profile a has only one peak. If so, the variables P1a, P2a, and V1a are set equal to each other in an operation 188. In either case, the image processing logic then examines profile b to determine whether it has only one peak, at the logic subsection 190. If profile b has only one peak, then the variables P1b, P2b, and V1b, are set equal to each other in an operation 192.

Continuing with FIG. 7c therein, a feature F8, which is the average value of the two valleys subtracted from the average value of the four peaks of the two profiles of the cell, is determined by subsection 194. Then the cell feature F1 is examined to determine whether the size of the cell is larger than a threshold T8 at a logic subsection 196.

If the cell is large, i.e., F1 is greater than T8, it is possible that the cell is a target cell despite the previous target cell analysis and therefore another target cell analysis will be performed beginning in operation 198.

Therein, a variable LEV3 is set equal to one-half the value of feature F8 (operation 198).

Next, a search for the central pallor of the cell is initiated by searching a direction along the line from the top pixel of the cell through the center of the cell looking for a threshold condition, i.e., hitting a pixel which is below the threshold LEV3, before the center is reached. The chain code is then formed for the central pallor boundary (operation 202). The pallor circularity feature F9 is then computed in an operation 204. F9 is calculated as the number of pallor boundary pixels squared divided by the area of the central pallor. F9 is then compared to a threshold value T9 at a logic subsection 206 to determine the circularity of the central pallor. This operation is necessary since the two profiles from the previous target cell analysis may have missed the central area as shown for the cell 208. Thus, if circularity feature F9 is greater than the threshold T9, then the cell is a target cell, otherwise the cell is forwarded to the operation 209 wherein a feature relating to the size of the central pallor of the cell is computed.

The central pallor feature is defined as the percentage volume of a cylinder, with the height and area of the cell under consideration, not occupied by hemoglobin. this is illustrated in FIG. 8, where T represents the cell height or thickness, and 132 indicates the indented central pallor region. The cell area is known from previous analysis on that cell, i.e., F1. Also, feature F5 is the sum of the grey levels for pixels enclosed by the chain code defining the boundary of the cell. As noted above, the hemoglobin density is related to the thickness of the cell and in this manner the hemoglobin feature F5 defines a volume of the cell. The cylinder height, or thickness (T), is derived by using the average value of the peaks of the two thickness/density profiles of the cell as:

$$T = \frac{P1a = P2a + P1b + P2b}{4}$$

Thus, the volume of the central pallor may be calculated as: T times the area of the cell (F1) minus the hemoglobin content. Finally, the percentage pallor volume F6 is:

$$F6 = \frac{(T \times F1 - F5)}{T \times F1} \times 100\%$$

After this feature has been computed, the image processing logic proceeds to a logic subsection 210 wherein the cell is distinguished between bioconcave cells (C1) and spherocyte cells (C2) as it has already been determined that the cell is not an elongated cell (C3), an irregular cell (C4), or a target (C5). The logic subsection 210 compares the percentage pallor volume feature F6 to a threshold value T10 and the pallor depth feature F8 to a threshold T11 and if either feature is less than its associated threshold then the cell is deemed a spherocyte cell (C2), otherwise it is a bioconcave cell (C1).

Referring back to FIG. 5, the feature extraction operation 76 and the cell subpopulation classification operation 78 have been completed for the cell that had been located in the image scan. The image processing logic will then continue scanning the image for another cell (operation 66) and if no other cells are found then the features for those cells located as well as the cells' subpopulation classifications will be sent to the master control logic in the operation 80.

While the determination of the various features and decisions contained in the logic diagram of FIGS. 7a, 7b, and 7c is carried out utilizing the threshold values contained in Table V, it should be understood that the threshold values are based upon empirical and statistical analysis and can be varied somewhat without appreciably affecting the eventual classification of the cells. It should also be appreciated that the threshold values are believed to be optimum values which have been fixed to maximize the accuracy of the classification.

TABLE V

| Threshold | Value | Description |
|---|---|---|
| T1 | $6^2$ | Size threshold for artifact |
| T2 | $54^2$ | Size threshold for double cells |
| T3 | 25 | Elongated threshold |
| T4 | 16 | Cell circularity threshold |
| T5 | 7 | Spiculed threshold |
| T6 | 25 | Elongation threshold |
| T7 | 5 grey levels | Target center peak height threshold |
| T8 | $47^2$ | Size threshold for target cells |
| T9 | 20 | Pallor circularity threshold |
| T10 | 11% | Pallor volume threshold |
| T11 | 8 grey levels | Depth of pallor threshold |

Upon completion of the feature extraction and cell classification analyses for the cells located in the image, these features are transmitted to the master control logic as illustrated in FIG. 5. After acknowledging the receipt of the data (operation 82), the master control logic proceeds to update subpopulation measurements for each cell class located in the image just analysed (operation 84). A diagram illustrating the updating operation in greater detail is shown in FIG. 13. A plurality of accumulators are provided to produce a running total of a plurality of measurements for the cell subpopulations or classes. Each accumulation is a function of one or more cell features, such as the cell feature value itself or the value squared, for example. The cell feature values F1, F2, F4, F5, and F6 for a particular cell are provided as inputs to the accumulators together with the cell classification $C_i$ to which the cell features pertain. After the measurements for the cell have been accumulated, then the other cells in the image are similarly processed to further accumulate the measurements based on all of the cell's features.

Thus, the feature F2 (cell circularity feature) is provided at a line 212 to an accumulator 214. The accumulator 214 produces a running total S1, i.e., accumulates the measurement $(F2-14.1)^3$ for all the cells located by the image processing in logic wherein F2 is the cell circularity feature (Table IV). This measurement is used in a later calculation which provides a parameter describing the skewness of the distribution of all the red blood cells located with respect to the circularity feature of the cells.

Also, accumulated is the elongation feature F4 which is provided at a line 216 to accumulators 218 and 220. The accumulator 218 sums the total (S2) of the feature F4 for all the cells which is used to calculate the average elongation for the cells. The accumulator 220 provides a sum or running total (S3) of the elongation feature F4 squared, i.e., $(F4)^2$, which is used to calculate a parameter describing dispersion, or variation of the distribution of the red blood cells with respect to the mean of the elongation feature F4.

In the aforesaid copending application, not all feature measurements were accumulated for each subpopulation. For example, in that application the feature F6 (pallor volume) was only accumulated for the biconcave cells (subpopulation C1) and the spherocyte cells (subpopulation C2). Therefore, in addition to the features for a particular cell, the subpopulation classification for the particular cell to which the features pertain was provided as shown as $C_i$ at line 222. A plurality of logic utilize the input $C_i$ to discriminate among the cell subpopulations. Thus, the cell classification $C_i$ is provided to the inputs of a logic AND gate 224 and an AND gate 226 with subpopulation C1 constant (i.e., a 1) provided to the other input of the AND gate 224 and subpopulation C2 constant (i.e., a 2) provided to the othe input of AND gate 226. The output of these AND gates are provided to on OR gate 228 which may enable the accumulators 230 and 232. The accumulator 230 provides a summation of the feature F6 (central pallor volume) as indicated by input lines 242, but only when enabled by the logic OR gate 228. Similarly, the accumulator 232 accumulates the sum of the feature $(F6)^2$ but only when enabled. Thus, the gates 224, 226, and 228 permit the accumulators 239 and 232 to accumate the measurements derived from the feature F6 only when the feature had been extracted from a C1 or C2 biconcave or spherocyte class cell. The output of the accumator 232 is provided at S5 which is used to compute the dispersion parameter of the distribution of spherocyte and biconcave cells with respect to the mean volume of the central pallor of the cells. The output of the accumulator 230 is provided at S4 which is also used to calculate the dispersion parameter and also to calculate the mean or average central pallor volume for the spherocyte and biconcave cells.

Similarly, a logic AND gate 234 enables accumulators 236, 238, and 240 when $C_i$ at line 222 is equal to a 2, i.e., the cell features appearing on the feature lines 244 and 246 were extracted from a class C2 (spherocyte) cell. The accumulator 236 accumulates the feature F1 (cell area) which is provided at S11, which will be used to calculate the mean cell area parameter for the cells in the C2 classification. The accumulator 238 provides at S12 the accumulated total of feature F5 (cell hemoglobin content) which is used to calculate the mean cell hemoglobin content for the class C2. The accumulator 240 provides a total of the number of cells in the C2 class, i.e., N2 equals the number of spherocyte cells located by the image processing logic.

In a similar manner the total cell area for the elongated (C3), the irregular (C4), and target (C5) cells are provided at S13, S15, and S17, respectively. The total of all cells' hemoglobin content for the elongated, irregular, and target cells is provided at S14, S16, and S18, respectively. The total number of cells in each of the above subpopulations is provided at N3, N4, and N5.

Likewise, the total of all of the cells' areas for the biconcave subpopulation is provided at S6, the total of all the cells' hemoglobin contents is provided at S7, and the total number of biconcave cells is provided at N1. For additional accumulated measurements on the biconcave subpopulation, additional logic gates permit accumulators to discriminate among the class cells. Thus, an AND gate 248 enables accumulators 250, 252, and 254 when the features appearing at the lines 244 and 246 have been extracted from a C1, i.e., a biconcave cell.

The accumulator 250 provides the accumulated sum of the measurement $(F1)^2$ at S8. The accumulator 252 similarly provides the accumulated total of the measurement $(F5)^2$ at S9. Finally, the accumulator 254 provides the accumulated sum of the product of the feature F1 times the feature F5 $(F1 \times F5)$. The accumulated S9 and S10 are used to calculate parameters descriptive of the dispersion, or variation of the bivariate distribution which will be further explained hereinafter.

Thus the features for each cell examined by the image processing logic provide the inputs to the logic described in FIG. 13 for updating or accumulating measurements based upon the cell features with the particular measurements updated for each cell depending upon the subpopulation classification to which that particular cell belongs. The measurements updated by the logic of FIG. 13 may be used as an intermediate step for the calculation of parameters which are descriptive of each subpopulation classification as well as parameters which are descriptive of multivariate distributions of cell subpopulations with respect to different cell features.

Referring back to FIG. 5, it is seen that at logic subsection 80 the determination is made whether a preset total of N cells have been processed. If not, the master control logic returns to operation 58 wherein it waits for the "digitizing done" signal indicating that the image processing logic has completed digitizing the next field. If N cells have been processed, e.g., N=one thousand, then the accumulated measurements which had been updated as illustrated in FIG. 13 for those N cells are used to calculate the parameters descriptive of the subpopulations (operation 90) which is illustrated in greater detail in FIGS. 14a through 14e.

A parameter for the mean central pallor volume (PAL) of the biconcave and spherocyte cells is provided by a logic subsection 264 having inputs N1 (the number of biconcave cells), N2 (the number of spherocyte cells), and S4 (the accumulated sum of the volumes of the central pallors of those subclassifications). A parameter of the distribution of the biconcave and spherocyte cells with respect to the central pallor volume, herein, the central pallor volume standard deviation (PSD) is provided by a logic subsection 266 having inputs S4 and S5 and a logic subsection 268 which takes the square root of the output provided by the logic subsection 256 to finally produce the parameter PSD in a manner similar to that of the parameter ESD.

Figure 14C:
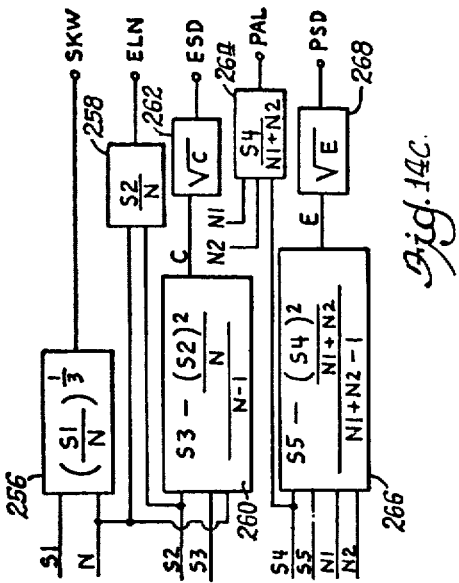
Figure 14A:
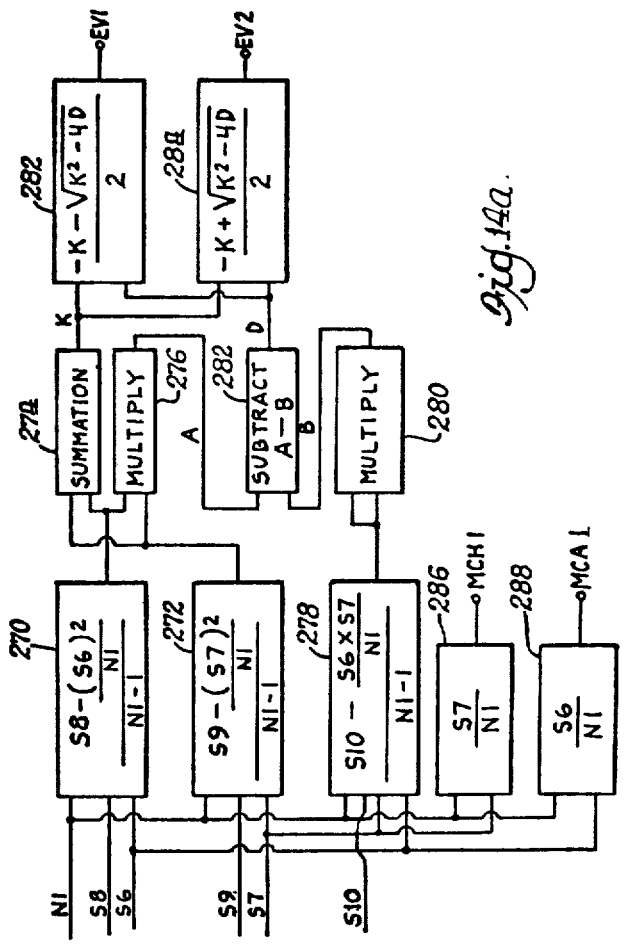

Referring to FIG. 14a, a logic diagram is shown for the computation of the parameters EV1 and EV2. The general formula for computing the variance of a distribution with respect to a variable is similar to that given for the standard deviation. The variance of the distribution with respect to cell area is provided by a logic section 270 which has inputs N (the number of biconcave cells), S8 (the summation of $(F1)^2$ for each biconcave cell), and S6 (the summation of F1 for each biconcave cell). The variance of the distribution with respect to hemoglobin content is provided by a logic section 272 which has inputs N1, S9 (the summation of $(F5)^2$), and S7 (the summation of (F5)). A logic section 274 provides the sum K of the output of the logic sections 270 and 272 and a logic section 276 provides the product A of the output of the logic sections 270 and 272.

The covariance of the distribution with respect to both the cell area and the cell hemoglobin content is provided by a logic section 278 having inputs N1, S7, S6, and S10 (the summation of the product F1 times F5 for each biconcave cell). A logic section 280 squares the utput of the logic section 278 to produce an output B. . logic section 282 subtracts the output A of the logic :ction 276 from the output B of the logic section 280 to rovide an output D. K and D are coefficients of a uadratic equation wherein a logic section 282 produces 1e first solution, EV1, to the quadratic equation, and 1e logic section 284 produces the second solution, :V2, to the equation.

A logic section 286 produces the mean cell hemogloin parameter for the biconcave cells by dividing the otal hemoglobin content S7 for all the biconcave cells y the number (N1) of the biconcave cells. The means ell area (MCA) of the biconcave cells is produced by a ogic section 288 which divides the total cell area (S6) f the biconcave cells by the total number (N1) of the iconcave cells.

Figure 14B:
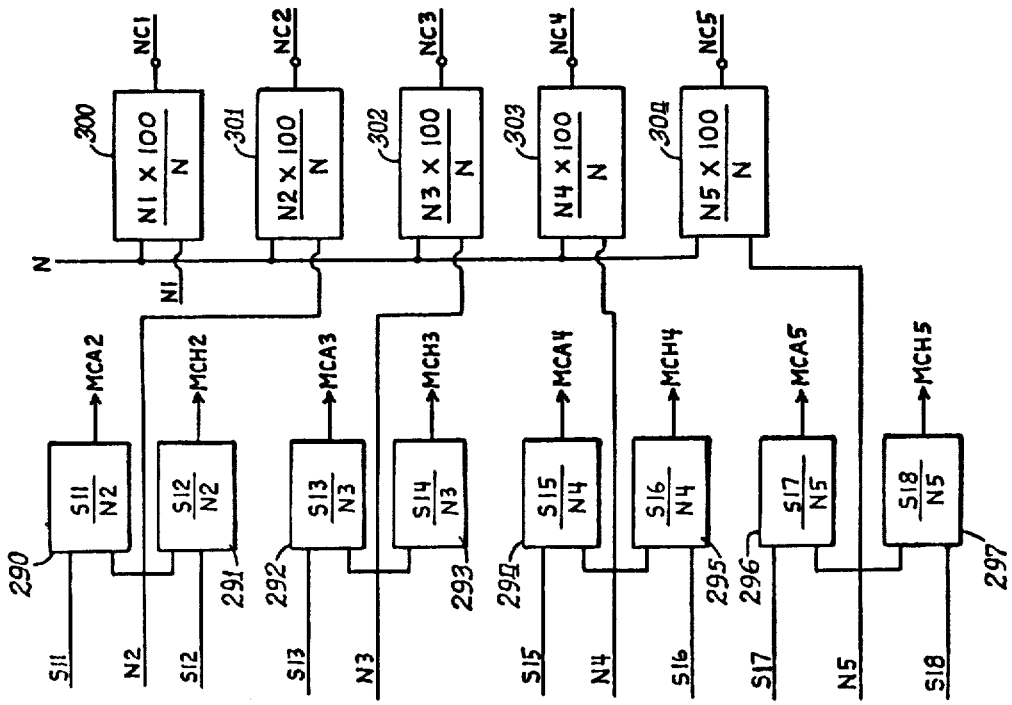

In a similar manner, as shown in FIG. 14b, the mean ell area and mean cell hemoglobin parameters are comuted for the remaining four classes or subpopulations, .e., the spherocytes, elongated, irregular, and target ells by either logic sections 290–297. The number of ells in each subpopulation, N1-N5, are each transormed into a percentage of the total number of cells by ive logic subsections 300–304, in FIG. 14b. For examle, the percentage of biconcave cells (NC1) is provided y logic subsection 300 which divides the number of iconcave cells (N1) by a total number of cells located y the image processing means (N) and multiplies by 100.

Finally, in the preferred embodiment, two other parameters are calculated which describe the entire population of cells analyzed as illustrated in FIGS. 14d and 14e. First, a mean cell area parameter (MCA) is calculated as a weighted average by multiplying the percentage of a subpopulation (i.e., NC1-NC5 being first divided by 100) by the mean cell area for that subpopulation for each subpopulation and adding the products to produce the weighted average. For example, the percentage of biconcave cells (NCl) is multiplied by the mean cell area (MCA1) for the biconcave subpopulation by means of a logic section 306 and the percentage of the spherocyte cells (NC2) is multiplied by the mean cell area of the spherocyte cells (MCA2) by means of a logic section 308 and so on for the other subpopulations and adding these five products by means of a summation logic section 310 to produce the mean cell area (MCA) for the entire population. A weighted average of the hemoglobin content for the entire population (MCH) is produced in a similar manner by a plurality of "mutiply" logic sections 312–316 and a summation logic section 318.

As explained hereinbefore, the general method of measuring the mean cell size to provide the close correlation to the MCVs achieved by the Coulter counter, is shown in FIG. 15. The logic section shown in FIG. 14 thus will receive as inputs the MCA over line 512 from FIG. 14d, the MCH over line 511 from FIG. 14e, and the PAL over line 510 from FIG. 14c. More specifically, the output for the pallor volume PAL may be applied from FIG. 14c as input to a multiplier logic section 400 (FIG. 15) which also receives an input factor −K3 to provide a calculation in form of an output on line 401 leading to the accumulator 403. Since the pallor volume is a negative value it will be subtracted in the accumulator 403. Likewise, the mean cell areas MCA for the entire population from logic section 310 in FIG. 14d is applied over line 512 as input to a multiplier logic section 405 (FIG. 15) along with the input factor K2 to provide an output of their product to the accumulator 403. The mean cell hemoglobin (MCH) provided over line 511 from summation logic 318 (FIG. 14e) serves an input ot a multiplier logic section 411 along with a factor K2 to provide an output to the summation logic 403. The output of the summation logic 403 is applied over a line 413 to an adder 415 to which is also applied an input factor K4 which is the offset factor. The output from the adder logic 415 is the mean cell volume for the total population of cells. Typically, the mean cell volume is reported at 430 by printing it out on a form or by displaying it on a cathode ray tube.

In a like manner the computation of mean cell volume (MCV) for a subpopulation of cells can be computed for any given subpopulation of cells. For instance, the biconcave cells are separately classified in the example given herein and in the aforesaid application. More specifically, the mean cell area (MCA 1) for the biconcave cells is provided by logic section 288 in FIG. 14a and this may be applied as an input on line 512 of FIG. 15. Likewise, the mean cell hemoglobin (MCH 1) for the biconcave cells is provided from logic section 286 (FIG. 14a) and this may be applied as an input on line 511 of FIG. 15. The mean central pallor volume (PAL) for the biconcave cells is available from logic section 264 in FIG. 14c and this may be applied as input over line 510 to the multiplier logic section 400 in the logic shown in FIG. 15. The respective constants will be applied as K1, K2 and K3 to the respective multiplier logic sections 405, 411 and 400. The remaining operation of the logic section shown in FIG. 15 will be as above described above to provide an output which is the mean cell volume (MCV) for the biconcave subpopulation of cells.

The logic section shown in FIG. 14d may also be used with various other subpopulations of cells to provide mean cell volume data for various abnormal cell populations. Because such data has not been heretofore available, there is a whole new data base for diagnosis of cell disorders, blood diseases or of cell morphological changes. For such abnormal cell populations it is preferred to generate for each cell its cell volume, its hemoglobin, and its pallor measurement and then after the cells are classified to accumulate in logic sections these values and then determine the mean cell area (MCA), mean cell hemoglobin (MCH), and mean central pallor volume (PAL). After this, a logic section, such as shown in FIG. 15 is used to provide a mean cell volume report or output for a given abnormal cell population.

The constants K1, K2, K3 and K4 are exemplary of the constants which may be used and these constants have been derived for red blood cells which have been spread by a spinner and then dried before image analysis, as above described. The factors tested herein automatically take into account the cell distortion due to drying of the cells prior to examination. On the other hand, if the red blood cells where kept wet and analyzed, e.g. while in a liquid stream, the constants would be different in order to adjust the mean cell volumes to that achieved by another piece of equipment such as a Coulter Model S counter. Of course, for the MCV of the present invention to accurately correspond to the MCV obtained by a Wintrobe process, the constants would be different as the Coulter counter MCV and the Wintrobe MCV for a given blood specimen will vary. Whether the Coulter counter or the Wintrobe process gives a more true and more accurate depiction of the MCV is not known. It is clear however, that neither the Coulter nor the Wintrobe processes analyze the mean cell pallor of individual cells, as can be done with the present invention, and use such central pallor data in calculating the MCV for a given red blood cell specimen.

The factors K1, K2, K3, and K4 were obtained by using a standard multiple linear regression technique as described fully in a publication entitled Numerical Method For Scientists and Engineers by R. W. Hamming, published by McGraw Hill in 1962, and by using the mean cell volume data for the same blood specimens as had been previously measured with a Coulter Model S counter. Other techniques such as comparison of data obtained emperically, may be used to develop a correlation between the image analysis mean cell volumes and the mean cell volumes obtained with a conventional mean cell volume measuring technique such as the Wintrobe technique or the electrical impedance technique of Coulter.

It is to be recognized that equipment has been developed other than that described herein, which measures by image analysis and which provides a cell size output in terms such as microcytic, normocytic, or macrocytic rather than the preferred size output report of a mean cell volume measurement. It is understood however that such equipment has not beeen accurate in that the results obtained were not consistent with the results obtained by conventional equipment which provides an MCV output. The present invention may easily provide such a classification of cells. For instance, the output from logic section 415 may be used to classify cells as microcytic, normocytic or macrocytic by having the output of logic section 415 applied to a logic section (not shown) having three levels with MCV below a given level being classified as microcytic, with the MCV's in a central range as normocytic, and with the MCV's above an upperlevel of the normocytic range being classified as macrocytic.

On the other hand, the size or volume information already being generated by such equipment may be correlated to that of conventional equipment producing MCV data by using the techniques herein disclosed. Thus, the present invention is not to be construed as being limited to the equipment herein described or to equipment that provides an output only in the terms of mean cell volume (MCV).

In both U.S. Pat. No. 4,097,845 and in copending application Ser. No. 875,126 it is pointed out that hard wired logic can be used or that a computer could be used and a specific computer was identified and a long computer program was attached as part of the specification. The computer programs already provided in those disclosures and the information in this disclosure will provide a description sufficient to one skilled in the art to enable the making of a program without undue additional work or experimentation. Hence, the inclusion of another program is submitted not to be warranted and to only result in additional and superfluous material. The present invention likewise may be made in hard wired form without such a computer program and hence the need for a computer program is superfluous for that reason also.

From the foregoing, it will be seen that the present invention provides a new and improved method and apparatus for generating cell size information correlated with cell size information such as mean cell volumes generated with conventional equipment. Although the cell size information may be reported out as placing the cells in a given size category such as microcytic, normocytic, or macrocytic, it preferably provides a mean cell volume output. Additionally, the present invention may be used to provide such size information for a subpopulation of red blood cells.

What is claimed is:

1. Apparatus for producing a signal representing the mean cell volume from a specimen of red blood cells, some of which have central pallors, said apparatus comprising:
    means for generating signals representative of the area of the cells;
    means for measuring the optical density of the individual cells and for generating signals representative of the hemoglobin content or mass of said cells;
    means for generating signals representative of the central pallor of the cells having central pallors; and
    means for generating an output representative of the mean cell volume of said cells using said representative area signals, hemoglobin signals, and central pallor signals.

2. An apparatus in accordance with claim 1 in which a means provides an offset factor for use by said means for generating an output representative of the mean cell volume.

3. An apparatus in accordance with claim 2 in which means generates for each of said area, hemoglobin and central pallor signals a predetermined proportional weight signal for weighting each of said signals by a predetermined value.

4. An apparatus in accordance with claim 1 in which said means for generating signals representative of the cells having central pallors comprises means for determining central pallor as a percentage of the volume of indentation of a cell.

5. An apparatus in accordance with claim 1 in which said means for generating an output representative of the mean cell volume of said cells comprises means for multiplying each of said representative area signals, hemoglobin signals, and central pallor signals by a proportional weight value, means for summing the products of said multiplications, and means for adding an offset factor to said sum from said last-mentioned means.

6. A method for producing a signal representing the mean cell volume from a specimen of red blood cells, some of which have central pallors with automated equipment having means for measuring cell area and means for measuring optical density, said method comprising the steps of:
    measuring the area of cells with said cell measuring means and generating signals representative of the area of the cells;
    measuring the optical density of the individual cells with said optical density measuring means and generating signals representative of the hemoglobin content or mass of said cells;
    generating signals representative of the central pallor of the cells having central pallors; and
    generating an output representative of the mean cell volume of said cells using said representative area signals, hemoglobin signals, and central pallor signals.

7. A method in accordance with claim 6, in which the step of generating an output representative of the mean cell volume includes the step of using an offset factor to compensate for drying of the red blood cells.

8. A method in accordance with claim 7, including the further step of generating for each of said area, hemoglobin and central pallor signals a predetermined proportional weight signal for weighting each of said signals by a predetermined value.

9. A method in accordance with claim 6, in which the step of generating signals representative of the cells having central pallors comprises the further step of:
determining central pallor as a percentage of the volume of indentation of a cell.

10. A method in accordance with claim 6, in which the step of generating an output representative of the mean cell volume of said cells comprises the further steps of:
multiplying each of said representative area signals, said hemoglobin signals, and said central pallor signals by a proportional weight value;
summing the products of said multiplications; and
adding an offset factor to said sum from said last-mentioned multiplication step.

11. A method of determining the mean cell volume of red blood cells of a particular subpopulation from a blood specimen with automated equipment having means for examining red blood cells, comprising the steps of:
examining a plurality of red blood cells in the blood specimen with said means for examining red blood cells,
classifying individual red blood cells by multiple respective features including shape and central pallor into a plurality of subpopulations; and
determining the mean cell volume for a given subpopulation of red blood cells.

12. A method of determining the mean cell volume of red blood cells of a particular subpopulation from a blood specimen with automated equipment having means for examining red blood cells, comprising the steps of:
examining a plurality of red blood cells in the blood specimen with said means for examining red blood cells,
classifying individual red blood cells by multiple respective features including shape and central pallor into a plurality of subpopulations;
determining the mean cell volume for a given subpopulation of red blood cells, and
examining the central pallors of the red blood cells and determining the mean cell volume for a subpopulation of cells having central pallors by using the central pallor measurement as a negative indentation value.

13. A method of determining the mean cell volume of red blood cells of a particular subpopulation from a blood specimen with automated equipment having means for examining red blood cells, comprising the steps of:
examining a plurality of red blood cells in the blood specimen with said means for examining red blood cells,
classifying individual red blood cells by multiple respective features including shape and central pallor into a plurality of subpopulations;
determining the mean cell volume for a given subpopulation of red blood cells,
generating a mean cell area measurement and a mean cell hemoglobin measurement and a mean cell pallor measurement;
multiplying each of these measurements by a predetermined and respectively different weight value,
summing the products of these multiplications; and,
adding an offset factor to the mean cell volume for correlation purposes.

14. A method of determining the mean cell volume of red blood cells of a particular subpopulation from a blood specimen with automated equipment having means for examining red blood cells, comprising the steps of:
examining a plurality of red blood cells in the blood specimen with said means for examining red blood cells,
classifying individual red blood cells by multiple respective features including shape and central pallor into a plurality of subpopulations;
determining the mean cell volume for a given subpopulation of red blood cells,
determining the mean cell volumes of the subpopulations to provide a mean cell volume for the specimen; adjusting the main cell volume of the specimen by a correlation factor; and reporting a correlated mean cell volume for the specimen.

15. An apparatus for determining the mean cell volume of red blood cells of a particular subpopulation from a blood specimen, said apparatus comprising:
means for examining a plurality of red blood cells in the blood specimen;
means for classifying individual blood cells by their individual shape and pallor features into a plurality of subpopulations; and
means for determining the mean cell volume for a given subpopulation of red blood cells.

16. An apparatus for determining the mean cell volume of red blood cells of a particular subpopulation from a blood specimen, said apparatus comprising:
means for examining a plurality of red blood cells in the blood specimen;
means for classifying individual blood cells by their individual shape and pallor features into a plurality of subpopulations;
means for determining the mean cell volume for a given subpopulation of red blood cells; and
means for examining the central pallors of the red blood cells and determining the mean cell volume for a subpopulation of cells having central pallors by using the central pallor measurement as a negative indentation value.

17. An apparatus for determining the mean cell volume of red blood cells of a particular subpopulation from a blood specimen, said apparatus comprising:
means for examining a plurality of red blood cells in the blood specimen;
means for classifying individual blood cells by their individual shape and pallor features into a plurality of subpopulations;
means for determining the mean cell volume for a given subpopulation of red blood cells;
means for generating a mean cell area measurement and a mean cell hemoglobin measurement and a mean cell pallor measurement;
means for multiplying each of these measurements by a predetermined constant;
means for summing the products of these multiplications; and,
means for adding an offset factor to mean cell volume for correlation purposes.

18. An apparatus in accordance with claim 15, including
    means for determining the mean cell volumes of at least one subpopulation and
    means for reporting a mean cell volume for said subpopulation.

19. Apparatus for producing a signal representing the mean cell volume from a specimen of red blood cells some of which have central pallors, said apparatus comprising:
    means for examining said cells by image analysis;
    means for generating signals representative of the mean cell area for the cells examined by said examining means;
    means for modifying the mean cell area information signals of said cells to produce mean cell volume signals for correlation purposes; and
    means for generating from said mean cell volume signals an output representative of the mean cell volume range of said cells.

20. An apparatus in accordance with claim 19 in which said means for generating an output representative of the size range provides an output indicating that the cell size range is microcytic, normocytic or macrocytic.

21. A method of determining a cell volume classification of red blood cells from a blood specimen with automated equipment having image analysis means for examining red blood cells and means for reporting out cell size classification comprising the steps of:
    examining a plurality of red blood cells in the blood specimen by image analysis with said image analysis means;
    extracting area features and generating signals representative of the mean cell area of said cells;
    generating signals for adjusting the measured mean cell area to a correlated mean cell volume;
    determining a correlated cell volume classification for said cells;
    reporting out a correlated cell volume classification for said cells with said means for reporting out cell size classification.

22. An apparatus in accordance with claim 21 in which the step of determining a cell size classification comprises the further steps of classifying the cell size information as being representative of microcytic, normocytic or macrocytic cells.

23. A method of determining the mean cell volume of red blood cells from a blood specimen with automated equipment having means for examining red blood cells and means for measuring central pallors of the cells and means for measuring size and hemoglobin content of the cells, comprising the steps:
    examining a plurality of red blood cells in the blood specimen,
    examining individual blood cells by respective features thereof including central pallors,
    determining a central pallor measurement indicating the percent of volume indentation due to the central pallor,
    generating size information for said cells, generating hemoglobin information for said cells, and determining the mean cell volume for a given subpopulation of cells by calculating the volume using said hemoglobin and said size information and deducting the central pallor measurement due to central pallor indentation.

24. A method in accordance with claim 23, including determining the mean cell area for individual cells and determining the mean cell hemoglobin for individual cells.

25. Apparatus for producing a signal representing the mean cell size from a specimen of red blood cells some of which have central pallors, said apparatus comprising:
    means for generating signals representative of the area of the cells;
    means for measuring the optical density of the individual cells and for generating signals representative of the hemoglobin content or mass of said cells;
    means for generating signals representative of the central pallor of the cells having central pallors; and
    means for generating an output size classification representative of the mean cell size of said cells using said representative area signals, hemoglobin signals, and central pallor signals.

* * * * *